United States Patent
Zaworotko et al.

(10) Patent No.: US 10,870,665 B1
(45) Date of Patent: Dec. 22, 2020

(54) ORGANIC ANION LITHIUM IONIC COCRYSTAL COMPOUNDS AND COMPOSITIONS

(71) Applicants: Michael John Zaworotko, Limerick (IE); Naga Duggirala, Tampa, FL (US); Adam John Smith, Orlando, FL (US); Roland Douglas Shytle, Largo, FL (US)

(72) Inventors: Michael John Zaworotko, Limerick (IE); Naga Duggirala, Tampa, FL (US); Adam John Smith, Orlando, FL (US); Roland Douglas Shytle, Largo, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 16/553,626

(22) Filed: Aug. 28, 2019

Related U.S. Application Data

(63) Continuation of application No. 15/793,435, filed on Oct. 25, 2017, now Pat. No. 10,435,416, which is a continuation of application No. 14/779,774, filed as application No. PCT/US2014/034670 on Apr. 18, 2014, now Pat. No. 9,840,521.

(60) Provisional application No. 61/813,901, filed on Apr. 19, 2013.

(51) Int. Cl.
| | |
|---|---|
| *C07F 1/02* | (2006.01) |
| *A61K 45/00* | (2006.01) |
| *C07D 207/16* | (2006.01) |
| *A61K 45/06* | (2006.01) |
| *A61K 33/14* | (2006.01) |
| *A61K 33/00* | (2006.01) |
| *C07C 229/08* | (2006.01) |

(52) U.S. Cl.
CPC ............. *C07F 1/02* (2013.01); *A61K 33/00* (2013.01); *A61K 33/14* (2013.01); *A61K 45/06* (2013.01); *C07C 229/08* (2013.01); *C07D 207/16* (2013.01)

(58) Field of Classification Search
CPC .................. C07F 1/02; A61K 37/00
See application file for complete search history.

(56) References Cited

FOREIGN PATENT DOCUMENTS

WO    WO2012129568    9/2012

OTHER PUBLICATIONS

European Search Report dated Nov. 11, 2016; 4 pages; Application No. 14786024.1; European Patent Office, Munich German.
Tien Teng Ong, et al.; 2.1 Cocrystals of Homochiral and Achiral Amino Acid Zwitterions with u+ Salts: Water-Stable Zeolitic and Diamondoid Metal-Organic Materials; 4 pages; Journal of the American Chemical Society; 2011; pp. 9224-9226.
Debasis Banerjee, et al. "Synthesis and Structural Characterization of a 3-D Lithium Based Metal-Organic Framework Showing Dynamic Structural Behavior"; Crystal Growth & Design Article 2010, vol. 10, pp. 2801-2805.
Ismailova, G. M.; Mukhiddinova, N. A.; "Lithium complexes"; "C:\EPODATA\SEA\eplogf\extern$3.log"; 1997; 1 page.
Klale et al., "Challenges in Translational Development of Pharmaceutical Cocrystals," Journal of Pharmaceutical Sciences 2017, vol. 106, pp. 457-470.
Grecu et al., "Validation of Computational Cocrystal Prediction Tool: Comparison of Virtual and Experimental Cocrystal Screening Results," Crystal Growth and Design 2014, vol. 14, pp. 164-171.
Fraenkel et al., "Lithio( diphenylphosphino)methane-Tetramethylethylenediamine: Crystal Structure and NMR Studies of a Coordinatively Unsaturated, Monomeric Organolithium," Organometallics, vol. 8, No. 10, 1989, pp. 2308-2311.

*Primary Examiner* — Sikarl A Witherspoon
(74) *Attorney, Agent, or Firm* — Thomas|Horstemeyer, LLP

(57) ABSTRACT

A cocrystal having the formula LiX.aM, or a solvate or hydrate thereof, wherein X is a conjugate base of an organic acid, M is a neutral organic molecule, and a is from 0.5 to 4, pharmaceutical compositions comprising such cocrystals, cocrystal solvates, or cocrystal hydrates, and methods of preparing such cocrystals, cocrystal solvates, or cocrystal hydrates, and such pharmaceutical compositions.

19 Claims, 29 Drawing Sheets

ORGANIC ANION LITHIUM IONIC COCRYSTAL COMPOUNDS AND COMPOSITIONS

CROSS-REFERENCE TO RELATED APPLICATIONS

This application is a continuation of U.S. Utility Application entitled "ORGANIC ANION LITHIUM IONIC COCRYSTAL COMPOUNDS AND COMPOSITIONS", having Ser. No. 15/793,435, filed on Oct. 25, 2017, which is a continuation of U.S. Utility Application entitled "ORGANIC ANION LITHIUM IONIC COCRYSTAL COMPOUNDS AND COMPOSITIONS", having Ser. No. 14/779,774 (now U.S. Pat. No. 9,840,251), filed on Sep. 24, 2015, which is the 35 U.S.C. § 371 national stage application of PCT Patent Application entitled "ORGANIC ANION LITHIUM IONIC COCRYSTAL COMPOUNDS AND COMPOSITIONS", having serial number PCT/US14/34670, filed Apr. 18, 2014, which claims priority to and the benefit of, U.S. Provisional Patent Application entitled "ORGANIC ANION LITHIUM IONIC COCRYSTAL COMPOUNDS AND COMPOSITIONS", having Ser. No. 61/813,901, filed Apr. 19, 2013, all of which are herein incorporated by reference in their entirety.

FIELD OF THE INVENTION

The present invention generally relates to ionic cocrystal compounds and compositions containing a lithium salt and a neutral organic molecule in a stoichiometric ratio wherein the lithium salt comprises an organic anion salt of lithium. Such compositions may be used in the preparation of (or even as) lithium-containing pharmaceuticals, or for commercial/industrial uses such as green chemistry (synthesis of polymers and specialty chemicals), energy sustainability (low density porous materials), pesticides/herbicides, explosives/propellants and/or electronic materials.

BACKGROUND OF THE INVENTION

In 1800, lithium, in particular $LiCO_3$, was first used to dissolve bladder stones for the treatment of urate imbalances. In 1871, there marked the first recorded use of lithium for the treatment of mania. In 1886, there was recorded use of lithium carbonate (the active ingredient in the current pill form of lithium) to prevent depression. In 1929, lithium citrate was used in "Bib-Label Lithiated Lemon-Lime Soda", a beverage marketed as a cure for hangovers. In 1948, lithium was first used by psychiatrists to treat patients with mania, and in that same year, lithium citrate was removed from the beverage 7UP®. The following year marked lithium's first legitimate medical application, and in 1970 the FDA approved lithium for the treatment of mania. (http://www.psycheducation.org/depression/-meds/LithiumHistory.htm; Gielen, Marcel, Edward R. T. Tiekink (2005). *Metallotherapeutic drugs and metal-based diagnostic agents: The use of metals in medicine*. John Wiley and Sons. p. 3. ISBN 0-470-86403-6; and Gerhard N. Schrauzer. *Journal of the American College of Nutrition*, Vol. 21, No. 1, 14-21 (2002)).

Lithium salts have a long history of human consumption beginning in the 1800s. In psychiatry, they have been used to treat mania and as a prophylactic for depression since the mid 20th century (Shorter E. *The history of lithium therapy*. Bipolar Disord. 2009; 11 Suppl 2:4-9). Today, lithium salts are used as a mood stabilizer for the treatment of bipolar disorder. Although the FDA has approved no medications as safe and effective treatments for suicidality, lithium has also proven to be the only drug that consistently reduces suicidality in patients with neuropsychiatric disorders (Baldessarini R J, Tondo L, Hennen J. *Treating the suicidal patient with bipolar disorder. Reducing suicide risk with lithium*. Ann N Y Acad Sci. 2001; 932:24-38; discussion 9-43; Goodwin F K, Fireman B, Simon G E, Hunkeler E M, Lee J, Revicki D. *Suicide risk in bipolar disorder during treatment with lithium and divalproex*. JAMA. 2003; 290:1467-73).

Although suicide and suicidality are major and growing public health problems and suicide is now ranked as the 11th leading cause of death in the U.S., the relationship between psychiatric medication and suicidality has not been well studied. This is at a time when there is growing evidence that vulnerability to suicidality may be inherited independently of vulnerability to mood disorders. These considerations have led to increasing calls for a separate category for "Suicide Disorders" in DSM V. However, there is growing evidence that treatments that are effective for mood disorders are not always effective for suicidality and vice versa. Paradoxically, antidepressants, although they improve depression over 4 to 8 weeks, are not believed to lower suicidality. In contrast, lithium does appear to lower suicidality in both recurrent unipolar major depressive disorder and in bipolar depression but is not a good short-term treatment of depression. To date, no medication has been specifically approved by the US Food and Drug Administration (FDA) or by any of the world's regulatory agencies. Moreover, in the context of growing concern about suicide in the U.S., the FDA is has recently expressed interest in reviewing any medication that might demonstrate efficacy against suicidality if suicidality is the a-priori primary outcome measure. Lithium is the only medication that consistently reduces suicidality in recurrent unipolar major depressive disorder and in bipolar disorder. However existing lithium drugs such as lithium chloride and lithium carbonate suffer from chronic toxicity, poor physicochemical properties and poor brain bioavailability.

Despite these effective medicinal uses, current lithium pharmaceutics (lithium carbonate and lithium citrate) are plagued with a narrow therapeutic window that requires constant blood draws for the patient and monitoring of plasma lithium levels and thyroid hormones by a clinician. Many patients undergoing lithium therapy find the side effects to be unbearable, which negatively effects compliance and discourages physicians from utilizing lithium. These problems arise because the site of action for the treatment of psychiatric and neurodegenerative diseases are in the brain and lithium salts cross the blood-brain-barrier slowly (Davenport V D. *Distribution of parenterally administered lithium in plasma, brain and muscle of rats*. Am J Physiol. 1950; 163:633-41; Ebadi M S, Simmons V J, Hendrickson M J, Lacy P S. *Pharmacokinetics of lithium and its regional distribution in rat brain*. Eur J Pharmacol. 1974; 27:324-9). This often requires multiple administrations throughout the day to reach therapeutic concentrations. Unfortunately, this leads to peripheral accumulation of lithium resulting in metabolic adverse effects such as hypothyroidism, hyperparathyroidism, weight gain, and nephrogenic diabetes insipidus (Livingstone C, Rampes H. *Lithium: a review of its metabolic adverse effects*. J Psychopharmacol. 2006; 20:347-55).

Because lithium is so effective at reducing manic episodes in patients with bipolar disorder, it is still used clinically despite its narrow therapeutic index. This has led researchers to begin to look for alternatives to lithium with similar bioactivities. The problem with this approach is that the mechanism of action remains highly debated. However, recent studies have identified many important bioactivities of lithium that may be responsible for its therapeutic efficacy in its current FDA approved indications and beyond. Lithium exerts neuroprotective effects by increasing the phosphorylation of ERK (Pardo R, Andreolotti A G, Ramos B, Picatoste F, Claro E. *Opposed effects of lithium on the MEK-ERK pathway in neural cells: inhibition in astrocytes and stimulation in neurons by GSK3 independent mechanisms*. J Neurochem. 2003; 87:417-26). The extracellular signal-regulated kinase (ERK) pathway is important for mediating neurogenesis and synaptic plasticity and has been implicated as an important target for mood stabilizers (Chen G, Manji H K. *The extracellular signal-regulated kinase pathway: an emerging promising target for mood stabilizers*. Current opinion in psychiatry. 2006; 19:313-23). Lithium has also been found to inhibit enzymes that require metal ions for catalysis in a noncompetitive manner by displacing a divalent cation (Phiel C J, Klein P S. *Molecular targets of lithium action*. Annu Rev Pharmacol Toxicol. 2001; 41:789-813). Two of these enzymes that have important implications in bipolar disorder are glycogen synthase kinase-3 (GSK-3) and inositol monophosphatase. GSK-3 beta was first identified as the molecular target of lithium by Klein et al (Klein P S, Melton D A. *A molecular mechanism for the effect of lithium on development*. Proc Natl Acad Sci USA. 1996; 93:8455-9). It functions by phosphorylating glycogen synthase, the rate-limiting enzyme of glycogen biosynthesis (Alon L T, Pietrokovski S, Barkan S, Avrahami L, Kaidanovich-Beilin O, Woodgett J R, et al. *Selective loss of glycogen synthase kinase-3alpha in birds reveals distinct roles for GSK-3 isozymes in tau phosphorylation*. FEBS Lett. 2011; 585:1158-62). GSK-3 inhibitors like lithium generally produce a weak anti-depressant-like and strong anti-mania-like effect, which explains its utility in bipolar disorder (Rowe M K, Wiest C, Chuang D M. *GSK-3 is a viable potential target for therapeutic intervention in bipolar disorder*. Neurosci Biobehav Rev. 2007; 31:920-31). GSK-3 is expressed in all tissues, with particularly abundant levels in the brain (Yao H B, Shaw P C, Wong C C, Wan D C. *Expression of glycogen synthase kinase-3 isoforms in mouse tissues and their transcription in the brain*. J Chem Neuroanat. 2002; 23:291-7). Therefore, this enzyme has tremendous potential as a therapeutic target for the treatment of neurological diseases that are characterized by dysregulated GSK-3 such as Alzheimer's disease (AD) and HIV associated neurocognitive disorders (Anthony I C, Norrby K E, Dingwall T, Carnie F W, Millar T, Arango J C, et al. *Predisposition to accelerated Alzheimer-related changes in the brains of human immunodeficiency virus negative opiate abusers*. Brain. 2010; 133:3685-98; Avila J, Hernandez F. *GSK-3 inhibitors for Alzheimer's disease*. Expert Rev Neurother. 2007; 7:1527-33; Martinez A, Perez D I. *GSK-3 inhibitors: a ray of hope for the treatment of Alzheimer's disease?* J Alzheimers Dis. 2008; 15:181-91; Dewhurst S, Maggirwar S B, Schifitto G, Gendelman H E, Gelbard H A. Glycogen synthase kinase 3 beta (GSK-3 beta) as a therapeutic target in neuroAIDS. J Neuroimmune Pharmacol. 2007; 2:93-6).

In addition to inhibiting GSK-3, lithium also inhibits inositol monophosphatase (IMPase) leading to cerebral inositol depletion (Allison J H, Stewart M A. *Reduced brain inositol in lithium-treated rats*. Nature: New biology. 1971; 233:267-8). This has been gaining favor from some as the putative target of lithium therapy since its mechanism was elucidated by Pollack et al (Pollack S J, Atack J R, Knowles M R, McAllister G, Ragan C I, Baker R, et al. *Mechanism of inositol monophosphatase, the putative target of lithium therapy*. Proc Natl Acad Sci USA. 1994; 91:5766-70). Furthermore, lithium, valproic acid, and carbamazepine, which are all used for stabilization of mood, have been shown to lead to the depletion of inositol (Harwood A J. *Lithium and bipolar mood disorder the inositol-depletion hypothesis revisited*. Mol Psychiatry. 2005; 10:117-26). This has bolstered support for the inositol depletion hypothesis of lithium therapy and has highlighted this molecular target in the search for "lithium mimetics" (Singh N, Halliday A C, Thomas J M, Kuznetsova O V, Baldwin R, Woon E C, et al. *A safe lithium mimetic for bipolar disorder*. Nature communications. 2013; 4:1332). However, given the frequency of suicidality as a comorbidity in patients with bipolar disorder (Goodwin F K, Jamison K R. *Manic-depressive illness*. New York: Oxford University Press; 1990; Kilbane E J, Gokbayrak N S, Galynker I, Cohen L, Tross S. A review of panic and suicide in bipolar disorder: does comorbidity increase risk? Journal of affective disorders. 2009; 115:1-10) and that only lithium consistently reduces suicidality in these patients, it is doubtful that alternate IMPase inhibitors will produce the desired clinical outcome that can be achieved with lithium.

Crystal engineering is the understanding of intermolecular interactions in the context of crystal packing and utilization of such understanding in the design of new solids with desired physical and chemical properties. Cocrystals are solids that are crystalline single phase materials composed of two or more different molecular and/or ionic compounds (i.e. cocrystal formers) generally in a stoichiometric ratio. When one or both of the cocrystal formers are ionic (i.e., salts), the resulting cocrystal is an ionic cocrystal; when both of the cocrystal formers are molecular (i.e., molecules including zwitterionic molecules), the resulting cocrystal is a molecular cocrystal. A pharmaceutical cocrystal is a cocrystal in which a pharmaceutically acceptable cocrystal former forms a supramolecular synthon with an active pharmaceutical ingredient ("API") (Vishweshwar, P; McMahon, J. A.; Bis, J. A.; Zaworotko, M. J. "Pharmaceutical Co-Crystals." *J. Pharmaceutical Sciences*, Vol. 95, No. 3, 499-516, 2006). For example, Hoogsteen's cocrystal is the combination of 1-methylthymine (MTH) and 9-methyladenine (MAD) to form MTHMAD (Schmidt, J.; Snipes, W. *Int. J. Radiat. Biol.*, 1967, 13, 101-109; K. Hoogsteen, 1963, *Acta Crystallogr.*, 16, 907). Crystal forms are important to pharmaceutical science for their purity, processability, physiochemical properties, stability, reproducibility, and cost of delivery. Hundreds of cocrystal forms may exist for an active pharmaceutical ingredient and it may therefore be possible to exert control over solubility to attenuate serum concentration and increase bioavailability (Smith, A. J.; Kavuru, P.; Wojtas, L.; Zaworotko, M. J.; Shytle, R. D. "Cocrystals of Quercetin with Improved Solubility and Oral Bioavailability." *Molecular Pharmaceutics*, 8, 1867-1876, 2011).

Lithium remains widely prescribed by clinicians because of its efficacy and limited side effects despite its narrow therapeutic index (Halford, Bethany. "Limits of Lithium." *Chemical and Engineering News*, Vol. 91, Issue 12, 15-20, 2013). Plasma levels of lithium last for 12-24 hours depending on dosage, and typically there is no trace of LiCl in the plasma at 48 hours. Lithium influx into the brain is slow, with brain levels peaking at 24 hours following single oral dose. Constant plasma levels are required for more than 24 hours to equilibrate with plasma. The proposed mechanism of action of lithium and the mechanism of inhibitory regulation of GSK-3 activity by lithium have been described. (Chiu and Chuang (2010) Molecular actions and therapeutic potential of lithium in preclinical and clinical studies of CNS disorders. Pharmacol Ther.; 128(2): 281-304). Inhibitory regulation of GSK-3 activity by lithium is affected by magnesium (Ryves, Jonathan, et al., Lithium Inhibits Glycogen Synthase Kinase-3 by Competition for Magnesium, Biochemical and Biophysical Research Communications 280, 720-725 (2001)).

Ionic cocrystals of lithium salts with compounds known to be actively transported into the cerebrospinal compartment could preferentially distribute lithium to the brain. Ionic cocrystals of NaCl and sucrose were isolated in the late 1940s (Beevers, C. A., Cochran, W. *Nature.* 1946, 157, 872). However, the field is relatively unexplored, and medicinal uses have not been addressed in the prior art. The prior art has also seen ionic cocrystals formed from alkali metal bromides with barbituric acid (D. Braga et al., *Chem. Commun.*, 2010, 46, 7715-7717; *Cryst. Growth Des.*, 2011, 11, 5621-5627; *Chem. Commun.*, 2012, 48, 8219-8221). This and all other referenced publications are incorporated herein by reference in their entireties. Furthermore, where a definition or use of a term in a reference, which is incorporated by reference herein is inconsistent or contrary to the definition of that term provided herein, the definition of that term provided herein applies and the definition of that term in the reference does not apply.

SUMMARY OF THE INVENTION

Among the various aspects of the present invention may be noted the provision of compositions comprising a lithium ionic cocrystal of an organic anion and a neutral organic molecule in a stoichiometric ratio, and a method for generating ionic cocrystals that involve Li-carboxylate-Li linkages that can be formed when cocrystal formers such as amino acid zwitterions form cocrystals with lithium. The resulting compositions may be used, for example, in the preparation of (or even as) lithium-containing pharmaceuticals, or for commercial/industrial uses such as green chemistry (synthesis of polymers and specialty chemicals), energy sustainability (low density porous materials), pesticides/herbicides, explosives/propellants and/or electronic materials. In one such embodiment lithium compounds and compositions of the present invention require lower dosages to achieve therapeutic brain levels of lithium for psychiatric disorders, thus broadening lithium's therapeutic index.

Another aspect of the present invention is that the organic anion lithium ionic cocrystal compounds and compositions described herein offer improved physicochemical properties compared to existing forms of lithium and therefore have the potential to be developed as pharmaceuticals (as anti-suicidal drugs or for use against other mood disorders).

Briefly, therefore, one aspect of the present invention is an ionic cocrystal having the formula LiX.aM, wherein X is a conjugate base of an organic acid, M is a neutral organic molecule. In certain aspects, a can be from 0.5 to 4.

In another aspect, disclosed is a cocrystal having the formula LiX.aM.bS wherein X is a conjugate base of an organic acid, M is a neutral organic molecule, and S is solvent or water.

The present invention is further directed to an ionic cocrystal having the formula LiX.aM, or a solvate or hydrate thereof, wherein X is a conjugate base of an organic acid, M is a neutral organic molecule. In certain aspects, a can be from 0.5 to 4.

The present invention is further directed to a pharmaceutical composition comprising a compound having the formula LiX.aM or a solvate or hydrate thereof, wherein X is a pharmaceutically acceptable conjugate base of an organic acid, M is a neutral organic molecule, and a is from 0.5 to 4.

The present invention is further directed to a dosage unit form of a pharmaceutical composition, the dosage unit form comprising a compound having the formula LiX.aM or a solvate or hydrate thereof, wherein X is a pharmaceutically acceptable conjugate base of an organic acid, M is a neutral organic molecule, and a is from 0.5 to 4.

The present invention is further directed to a method for preparing an organic anion lithium ionic cocrystal compound comprising a lithium salt and a complementary neutral organic compound in a stoichiometric ratio wherein the lithium salt comprises an organic anion salt of lithium. The method comprises combining a lithium salt and a complementary neutral organic compound in a solvent, the lithium salt comprising a conjugate base of an organic acid, and evaporating or cooling the solvent to form the organic anion lithium ionic cocrystal. The stoichiometric ratio of the complementary neutral organic compound to the lithium salt in the organic anion lithium ionic cocrystal is preferably from 0.5:1 to 4:1, respectively.

Other aspects and objects of the invention will be in part apparent and in part pointed out hereinafter.

ABBREVIATIONS AND DEFINITIONS

Figure 1:
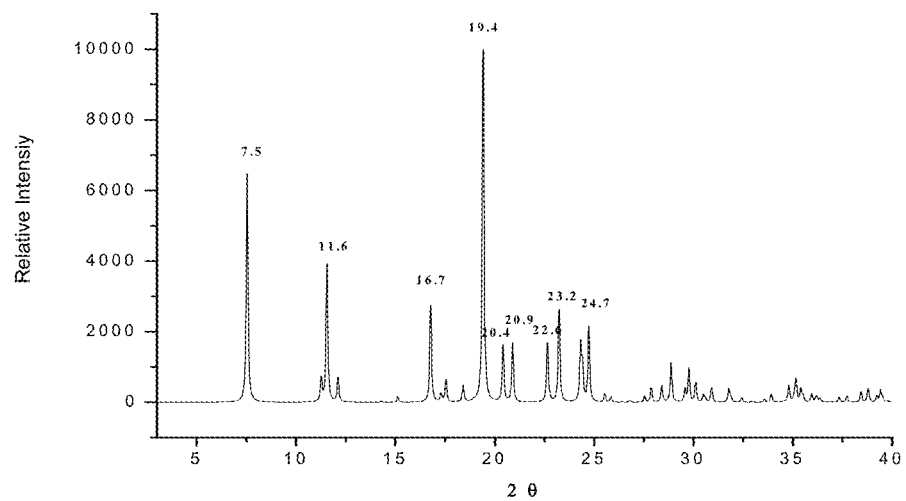
FIG. 1 is the calculated and experimental powder x-ray diffraction pattern of LBEPRO, as described further in Example 1.
Figure 1:
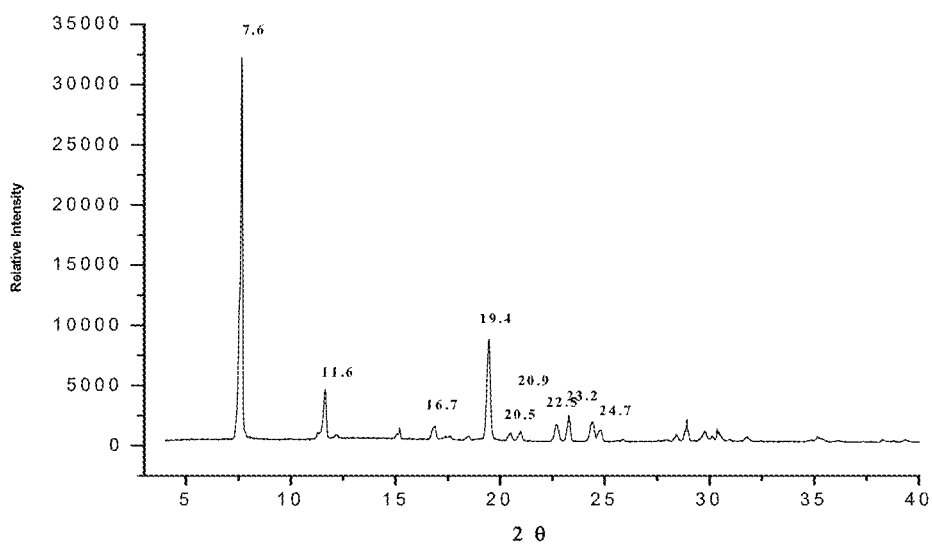

The following definitions and methods are provided to better define the present invention and to guide those of ordinary skill in the art in the practice of the present invention. Unless otherwise noted, terms are to be understood according to conventional usage by those of ordinary skill in the relevant art.

An "amino acid" as used herein refers to a molecule containing an amine group, a carboxylic acid group and a side-chain that varies between different amino acids.

A "cocrystal" as used herein refers to a multiple component crystal containing two or more non-identical compounds (cocrystal formers) in a stoichiometric ratio each of which is solid under ambient conditions (i.e., 22° C., 1 atmosphere of pressure) when in their pure form.

A "neutral" composition as used herein refers to a composition, or moiety, optionally possessing both cationic and anionic groups, having a zero net electrical charge.

An "organic acid" as used herein is an organic Bronsted acid.

An "organic anion" as used herein is a conjugate base of an organic acid.

A "weak organic acid" as used herein refers to an organic Bronsted acid having a pKa of about 0 to about 10.

A "zwitterion compound" or "zwitterionic composition" as used herein refers to a macromolecule, material, or moiety, possessing cationic and anionic groups, or acidic and basic centers that tautomerize to the corresponding cationic and anionic groups. Typically, and preferably in the context of the present invention, these charged groups are balanced, resulting in a material with zero net electrical charge.

DETAILED DESCRIPTION OF THE INVENTION

The present invention is generally directed to compounds and compositions comprising a lithium ionic cocrystal of a lithium salt and at least one complementary neutral cocrystal former (i.e., capable of coordinating lithium) in a stoichiometric ratio wherein the lithium salt comprises a conjugate base of an organic acid. Such compounds and compositions may be used as the active pharmaceutical ingredient in pharmaceutical compositions (optionally also including other components such as pharmaceutically acceptable excipients, diluents, nutritional supplements, and other additives as described elsewhere herein), or in other compositions having utility in applications in which lithium is desired.

In general, the organic anion lithium ionic cocrystal compounds and compositions are crystalline materials comprised of two or more unique (non-identical) compounds, each of which is solid at room temperature (i.e., 22° C.), in a generally stoichiometric ratio, each co-existing in the ionic cocrystal at the molecular level within the ionic cocrystal and each containing distinctive physical characteristics, such as structure, melting point and heats of fusion. The ionic cocrystals may also include water molecules, or one or more solvate molecules, in the crystalline lattice. Stated differently, solvates or hydrates of ionic cocrystals, or an ionic cocrystal further comprising a solvent, or water, or compound that is a liquid at room temperature, may be included in the compositions of the present invention. The water or solvate molecules can be included in the crystalline lattice in various ways. For example, the water or solvent molecules can be coordinated to the lithium in a stoichiometric ratio or can be found in voids in the crystalline lattice and be of variable stoichiometry, or both. In one embodiment, for example, an organic anion lithium ionic cocrystal compound or composition of the present invention, or solvate or hydrate thereof, has the formula LiX.aM.bS wherein X is a conjugate base of an organic acid, M is a neutral organic molecule, a is from 0.5 to 4, b is 0 to 3, and S is solvent or water.

In one exemplary embodiment, the organic anion lithium ionic cocrystal compound has the formula LiX.aM wherein X is a conjugate base of an organic acid, M is a neutral organic molecule, and a is from 0.5 to 4. For example, in one such embodiment, a is 0.5. By way of further example, in one such embodiment a is 1. By way of further example, in one such embodiment a is 1.5. By way of further example, in one such embodiment a is 2. By way of further example in one such embodiment a is 2.5. By way of further example, in one such embodiment a is 3. By way of further example, in one such embodiment a is 3.5. By way of further example, in one such embodiment a is 4.

In another exemplary embodiment, the organic anion lithium ionic cocrystal compound has the formula LiX.aM.bS wherein X is a conjugate base of an organic acid, M is a neutral organic molecule, a is from 0.5 to 4, and b is greater than 0. For example, in one such embodiment, b is 0.5. By way of further example, in one such embodiment b is 1. By way of further example, in one such embodiment b is 1.5. By way of further example, in one such embodiment b is 2. By way of further example in one such embodiment b is 2.5. By way of further example, in one such embodiment b is 3.

In another exemplary embodiment, the organic anion lithium ionic cocrystal compound or composition has the formula LiX.aM.bS wherein X is a conjugate base of an organic acid, M is a neutral organic molecule, a is 0.5, 1, 1.5, 2, 2.5, 3, 3.5, or 4, b is from 0, 0.5, 1, 1.5, 2, 2.5, 3, and S is solvent or water.

For pharmaceutical applications, it is generally preferred that the ionic cocrystals of the present invention comprise a pharmaceutically acceptable lithium salt and a stoichiometric amount of a second pharmaceutically acceptable molecule (the cocrystal former/neutral organic molecule) that is a solid under ambient conditions (i.e., 22° C., 1 atmosphere of pressure) wherein the pharmaceutically acceptable lithium salt comprises a pharmaceutically acceptable conjugate base of an organic acid. Although a number of cocrystals are within the ambit of this invention, exemplary cocrystals include organic anion lithium ionic cocrystals and neutral pharmaceutically acceptable zwitterionic compounds, flavonoids, xanthines, sugars, and/or polyphenols.

For non-pharmaceutical applications, the structures and properties of some organic anion lithium ionic cocrystal compounds or compositions mean that they are fine-tunable in terms of their composition and molecular recognition features. They can, therefore, be used for anion exchange or sequestration (storage) of small molecules such as hydrogen, methane and carbon dioxide. Notably, lithium is the lightest metal and the organic anion lithium ionic cocrystal compounds and compositions described herein are inherently air and water stable. They can also be prepared using homochiral organic compounds such as amino acids. They therefore offer a unique set of properties that collectively affords significant advantages over previous classes of porous material such as zeolites and metal-organic materials.

In an embodiment, non-aqueous, non-solvent impurities may be present in the organic acid lithium ionic cocrystal compound or composition. In general, it is preferred that the ionic cocrystal compound or composition contain less than 1% by weight impurities (i.e., compositions other than solvent and/or water that are solid at room temperature such as inorganic anion lithium salts) but in some embodiments impurities may constitute up to 5% by weight of the ionic cocrystal compound or composition if they are present as loosely bound guest molecules. In certain embodiments, a greater degree of purity may be desired; in such instances, it may be preferred that the ionic cocrystal compound or composition contain less than 0.5% by weight (non-aqueous, non-solvent) impurities. In some embodiments, it may be preferred that the ionic cocrystal compound or composition contain less than 0.1% by weight (non-aqueous, non-solvent) impurities. In other embodiments, it may be preferred that the ionic cocrystal compound or composition contain less than 0.01% by weight (non-aqueous, non-solvent) impurities.

Lithium Salts

In general, the lithium salt comprised by an ionic cocrystal composition of the present invention corresponds to the formula LiX wherein X is a conjugate base of an organic acid. In one such embodiment, X is a conjugate base of a weak organic acid. By way of further example, in one such embodiment X is a pharmaceutically acceptable conjugate base of a weak organic acid having a pKa in the range of about 0 to about 10. By way of further example, in one such embodiment X is a pharmaceutically acceptable conjugate base of a weak organic acid having a pKa in the range of about 2 to about 7. By way of further example, in one such embodiment X is a pharmaceutically acceptable conjugate base of a weak organic acid having a pKa in the range of about 3 to about 6. By way of further example, in one such embodiment X is a pharmaceutically acceptable conjugate base of a weak organic acid having a pKa in the range of about 3.5 to about 5.5.

In one exemplary embodiment, the lithium salt comprised by an ionic cocrystal composition of the present invention corresponds to the formula LiX wherein X is acetate, adipate, diacetate, alginate, aminosalicylate, anhydromethylenecitrate, arecoline, arginine, ascorbate, asparatete, benzenesulfonate (benzene), benzoate, bicarbonate, bisulfate, bitartrate, butylbromide, butyrate, calcium edentate, calcium edentate, camphorate, camsylate (camphorsulfonate), citrate, dihydrochloride, edentate, edisylate (1,2-ethanedisulfonate), estolate (lauryl sulfate), esylate (ethanesulfonate), fumarate, gluceptate (glucoheptonate), gluconate, digluconate, glucuronate, glutamate, glycerophosphate, glucollylarsanilate (p-glycollamidophenylarsonate), hexylresorcinate, hydrabamine (N,N'-di(dehydroabietyl)ethylenediamine), hydroxynaphthoate, isethionate (2-hydroxyethanesulfonate), lactate, lactobionate, lysine, malate, maleate, mandelate, mesylate, methylbromide, methylenebis (salicylate), methylnitrate, methylsulfate, mucate, napdisylate (1,5-naphthalenedisulfonate), napsylate, oxalate, palmitate, pamoate (embonate), pantothenate, pectinate, phenylethyulbarbiturate, picrate, polygalacturonate, propionate, saccharinate, salicylate, stearate, subacetate, succinate, disuccinate, disuccinate, tannate, tartrate, terephthalate, teoclate (8-chlorotheophyllinate), undecanoate, or xinafoate (1-hydroxy-2-naphthalenecarboxylate).

In another exemplary embodiment, the lithium salt comprised by a cocrystal composition of the present invention corresponds to the formula LiX wherein X is the conjugate base of acetylaminoacetic acid; N-acetyl-1-asparagine, N-acetylcystine, adamantoic acid, adipic acid, N-alkylsulfamates, anthraquinone-1,5-disulfonic acid, arabogalactan sulfate (arabino), arginine, aspartate, bis-2-carboxychromon-5-yloxy)alkanes, 4-chloro-m-toluenesulfonic acid, decanoate, diacetyl sulfate, dibenzylethylenediamine, diethylamine, diguiacyl phosphate, diocytyl sulfosuccinate, embonic (pamoic) acid, fructose 1,6-diphosphoric acid, glucose 1-phosphoric acid, glucose 6-phosphoric acid, 1-glutamine, hydroxynaphthhoate, lauryl sulfate, lysine, methanesulfonic acid, 2-naphthalenesulfonic acid, octanoate, probenecid, tannic acid, theobromine acetic acid, or 3,4,5-trimethoxybenzoate.

Cocrystal Formers/Neutral Organic Molecules

For pharmaceutical applications, it is generally preferred that the cocrystal former is any neutral organic molecule that may be safely administered to humans. Such compositions may be identified on the GRAS list (also known as the "Generally Recognized As Safe" list) or the EAFUS list (also known as the "Everything Added to Food in the United States" list) maintained by the U.S. Food and Drug Administration or excipients approved for pharmaceutical use. More typically, however, the cocrystal former/neutral organic molecule will be a pharmaceutically acceptable zwitterionic compound, sugar, polyphenolic compound, vitamin, xanthine, or flavonoid.

In one embodiment, the cocrystal former is a neutral zwitterionic compound. Exemplary zwitterionic compounds include nicotinic acids or naturally occurring or synthetic amino acids. For example, in one such embodiment, the cocrystal former comprises at least one of the 21 amino acids that are directly encoded for protein synthesis by the genetic code of eukaryotes, i.e., at least one of alanine, arginine, asparagine, aspartic acid, cysteine, isoleucine, glutamic acid, glutamine, glycine, histidine, leucine, lysine, methionine, phenylalanine, proline, selenocysteine, serine, taurine, threonine, tryptophan, tyrosine, and valine. For example, in one embodiment the cocrystal former is phenylalanine, leucine, tyrosine, or other amino acids that are preferentially transported into the brain as compared to other amino acids. By way of further example, in one embodiment the amino acid is an L-amino acid such as L-phenylalanine, L-leucine, or L-tyrosine. In an alternative embodiment, the amino acid is a D-amino acid such as D-phenylalanine, D-leucine, or D-tyrosine. In an alternative embodiment, the cocrystal former comprises a non-proteinogenic amino acid such as betaine.

In one embodiment, the cocrystal former may comprise an amino acid other than the 21 natural amino acids that are directly encoded for protein synthesis, such as non-standard amino acids and synthetic amino acids. Synthetic amino acids can include the naturally occurring side chain functional groups or synthetic side chain functional groups which modify or extend the natural amino acids with alkyl, substituted alkyl, cycloalkyl, heterocyclic, substituted heterocyclic, aryl alkyl, aryl, heteroaryl, heteroaryl alkyl, and like moieties as framework and with carboxyl, amine, hydroxyl, phenol, carbonyl, or thiol functional groups; exemplary synthetic amino acids include β-amino acids and homo or β-analogs of natural (standard) amino acids. Other exemplary amino acids include pyrrolysine, betaine, and carnitine.

In one embodiment, the cocrystal former is xanthine or a derivative thereof (known collectively as xanthines). Exemplary xanthines include caffeine, paraxanthine, theophylline and threobromine.

In one embodiment, the cocrystal former is a polyphenol. Exemplary polyphenols that may be used in the compositions of the present invention can be classified into the following categories: (1) phenolic acids, (2) flavonoids, (3) stilbenoids; (4) tannins, (5) monophenol such as hydroxytyrosol or p-tyrosol, (6) capsacin and other capsaicinoids and (7) curcumin. Phenolic acids form a diverse group including, for example, (a) hydroxycinnamic acids, e.g., p-coumaric acid, caffeic acid, and ferulic acid; (b) hydroxybenzoid acids, e.g., p-hydroxybenzoic acid, gallic acid, and ellagic acid; and (c) rosmarinic acid. Tannins are large molecules, found in red wine, tea, and nuts; the term is applied to any large polyphenolic compound containing sufficient hydroxyls and other suitable groups (such as carboxyls) to form strong complexes with proteins and other macromolecules and are usually divided into hydrolyzable tannins and condensed tannins (proanthocyanidins). At the center of a hydrolyzable tannin molecule, there is a polyol carbohydrate (usually D-glucose); the hydroxyl groups of the carbohydrate are partially or totally esterified with phenolic groups such as gallic acid (in gallotannins) or ellagic acid (in ellagitannins).

Flavonoids are a long and well-known class of natural product that is attracting increasing attention as nutraceuticals and pharmaceuticals. Flavonoids are based upon a group of compounds called chalcones and typically contain a 3-ring structure called flavone. The metabolic pathway in plants affords many derivatives including flavonols, flavan-3-ols, tannins and other polyphenolics. Flavonoids are synthesized and widely distributed in plants and fulfill many functions including pigmentation in flowers, and protection from attack by microbes and insects. The widespread distribution of flavonoids means that they are ingested in significant quantities by animals. Furthermore, their variety, their relatively low toxicity compared to, for example, alkaloids, and their biological activity (they can be anti-allergic, anti-inflammatory, anti-microbial, anti-cancer and they can improve cognitive functions) means that consumers, food manufacturers and pharmaceutical companies have become interested in flavonoids for their medicinal properties. Indeed, the beneficial effects of fruit, vegetables, and tea or even red wine have been attributed to flavonoid compounds. Although many flavonoids are abundant and commercially available they can be hard to purify and crystallize and their solubility can be low.

In one embodiment, therefore, the present invention is directed to cocrystals comprising a flavonoid as the cocrystal former. In this embodiment, for example, the cocrystal may comprise a flavonoid selected from the group consisting of resveratrol, epigallocatechin-3-gallate (EGCG), quercetin, ferulic acid, ellagic acid, hespereten, and protocatechuic acid. By way of further example, the cocrystal former may be a flavonoid selected from the group consisting of EGCG, ferulic acid, ellagic acid, hespereten, and protocatechuic acid.

In one embodiment, the present invention is directed to ionic cocrystals comprising a sugar as the cocrystal former. Exemplary sugars include monosaccharides and disaccharides. For example, in one embodiment the cocrystal former is selected from among fructose, galactose, glucose, lactitol, lactose, maltitol, maltose, mannitol, melezitose, myoinositol, palatinite, raffinose, stachyose, sucrose, trehalose, and xylitol.

In another preferred embodiment, the nutraceutical may be one of the previously mentioned flavonoid or a nutraceutical selected from a group of nutraceuticals currently believed to possess biological activity. For example, in this embodiment, the nutraceutical may be selected from the group consisting of vitamin B2 (riboflavin), glucosamine HCl, chlorogenic acid, lipoic acid, catechin hydrate, creatine, acetyl-L-carnitine HCl, vitamin B6, pyridoxine, caffeic acid, naringenin, vitamin B1 (thiamine HCl), baicalein, luteolin, hesperedin, rosmarinic acid, epicatechin gallate, epigallocatechin, vitamin B9 (folic), genistein, methylvanillin, ethylvanillin, silibinin, diadzein, melatonin, rutin hydrate, vitamin A, retinol, vitamin D2 (ergocalciferol), vitamin E (tocopherol), diosmin, menadione (K3), vitamin D3 (caholecalciferol), phloretin, indole-3-carbinol, fisetin, glycitein, chrysin, gallocatechin, vitamin B4 (adenine), vitamin B5 (pantothenic acid), vitamin B7 (biotin), theobromine, resveratrol, epigallocatechin-3-gallate (EGCG), quercetin, ferulic acid, ellagic acid, hespereten, and protocatechuic acid. By way of further example, in this embodiment, the nutraceutical may be selected from the group consisting of vitamin B2 (riboflavin), glucosamine HCl, chlorogenic acid, lipoic acid, catechin hydrate, creatine, acetyl-L-carnitine HCl, vitamin B6, pyridoxine, caffeic acid, naringenin, vitamin B1 (thiamine HCl), baicalein, luteolin, hesperedin, rosmarinic acid, epicatechin gallate, epigallocatechin, vitamin B9 (folic), genistein, methylvanillin, ethylvanillin, silibinin, diadzein, melatonin, rutin hydrate, vitamin A, retinol, vitamin D2 (ergocalciferol), vitamin E (tocopherol), diosmin, menadione (K3), vitamin D3 (caholecalciferol), phloretin, indole-3-carbinol, fisetin, glycitein, chrysin, gallocatechin, vitamin B4 (adenine), vitamin B5 (pantothenic acid), vitamin B7 (biotin), theobromine, quercetin, ferulic acid, ellagic acid, hespereten, and protocatechuic acid.

Cocrystal Formation

In general, organic anion lithium ionic cocrystal compositions of the present invention may be prepared by combining the lithium salt and the complementary neutral organic compound (i.e., the cocrystal former) in a solvent and using a commonly used method to promote crystallization such as evaporating or cooling the solvent.

In one embodiment, the lithium salt and the complementary neutral organic compound are combined in an aqueous system. Although not necessarily preferred, the lithium salt and complementary neutral organic compound may be dissolved in polar organic solvents such as acetone, acetonitrile, DMSO and alcohols.

In one embodiment, organic anion lithium ionic cocrystal compositions or the present invention may be prepared by combining a lithium-containing compound, an organic acid, and a complementary neutral organic compound, in a solvent, such as water, and using a commonly used method to promote crystallization such as evaporating or cooling the solvent.

Once formed, the solution is then preferably slowly cooled or solvent is slowly evaporated until the cocrystal is formed. The cocrystal structure of the resulting composition may be characterized by at least two techniques selected from the group consisting of powder x-ray diffraction, single crystal x-ray crystallography, differential scanning calorimetry, Fourier transform infrared spectroscopy and thermogravimetric analysis.

Pharmaceutical Forms

Pharmaceutical compositions of the present invention may comprise the active agent, i.e., a compound or composition comprising the organic anion lithium ionic cocrystal and a neutral organic compound in a stoichiometric ratio, alone or may include the active agent and any suitable additional component, such as one or more pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Each carrier is preferably acceptable in the sense of being compatible with the other ingredients of the formulation and not injurious to the patient.

Dosage unit forms of a pharmaceutical composition of the present invention comprise a desired amount of the active agent per dose unit and, if intended for oral administration, can be in the form, for example, of a tablet, a caplet, a pill, a hard or soft capsule, a lozenge, a cachet, a dispensable powder, granules, a suspension, an elixir, a dispersion, or any other form reasonably adapted for such administration. If intended for parenteral administration, it can be in the form, for example, of a suspension or transdermal patch. If intended for rectal administration, it can be in the form, for example, of a suppository. In one embodiment, the dosage unit form is a discrete dose form such as a tablet or a capsule suitable for oral administration, each containing a predetermined amount of the active agent.

Excipients employed in the compositions of the present invention may be solids, semi-solids, liquids or combinations thereof. In one embodiment, the excipient(s) is/are solids. Compositions of the invention containing excipients can be prepared by any known technique that comprises, for example, admixing an excipient with the cocrystal.

Compositions of the invention optionally comprise one or more pharmaceutically acceptable carriers or diluents as excipients. Suitable carriers or diluents illustratively include, but are not limited to, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioners sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of alpha- and amorphous cellulose (e.g., RexcelJ), powdered cellulose, hydroxypropylcellulose (HPC) and hydroxypropylmethylcellulose (HPMC); calcium carbonate; glycine; bentonite; block co-polymers; polyvinylpyrrolidone; and the like. Such carriers or diluents, if present, may constitute in total about 5% to about 99%, about 10% to about 85%, or even about 20% to about 80%, of the total weight of the composition. The carrier, carriers, diluent, or diluents selected may exhibit suitable flow properties and, where tablets are desired, compressibility.

Compositions of the invention optionally comprise one or more pharmaceutically acceptable disintegrants as excipients, particularly for tablet formulations. Suitable disintegrants include, but are not limited to, either individually or in combination, starches, including sodium starch glycolate {e.g., Explotab™ of PenWest) and pregelatinized corn starches {e.g., National™ 1551 of National Starch and Chemical Company, National™ 1550, and Colorcon™ 1500), clays {e.g., Veegum™ HV of R.T. Vanderbilt), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, may constitute in total about 0.2% to about 30%, about 0.2% to about 10%, or even about 0.2% to about 5%, of the total weight of the composition.

Pharmaceutical compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Such binding agents may also prevent or inhibit crystallization or recrystallization of a cocrystal of the present invention once the salt has been dissolved in a solution. Exemplary binding agents and adhesives include, but are not limited to, either individually or in combination, acacia; tragacanth; sucrose; gelatin; glucose; starches such as, but not limited to, pregelatinized starches (e.g., National™ 151 1 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™ of Aqualon); and ethylcellulose (e.g., Ethocel™ of the Dow Chemical Company). Such binding agents and/or adhesives, if present, may constitute in total about 0.5% to about 25%, about 0.75% to about 15%, or even about 1% to about 10%, of the total weight of the pharmaceutical composition.

Many of the binding agents are polymers comprising amide, ester, ether, alcohol or ketone groups and, as such, are optionally included in pharmaceutical compositions of the present invention. Exemplary binding agents include polyvinylpyrrolidones such as povidone K-30. Polymeric binding agents can have varying molecular weight, degrees of crosslinking, and grades of polymer. Polymeric binding agents can also be copolymers, such as block co-polymers that contain mixtures of ethylene oxide and propylene oxide units. Variation in these units' ratios in a given polymer affects properties and performance. Examples of block co-polymers with varying compositions of block units are Poloxamer 188 and Poloxamer 237 (BASF Corporation).

Compositions of the invention optionally comprise one or more pharmaceutically acceptable wetting agents as excipients. Such wetting agents may be selected to maintain the cocrystal in close association with water, a condition that may improve bioavailability of the composition. Such wetting agents can also be useful in solubilizing or increasing the solubility of crystals.

Non-limiting examples of surfactants that may be used as wetting agents in compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and degrees C. toxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, may constitute in total about 0.25% to about 15%, about 0.4% to about 10%, or even about 0.5% to about 5%, of the total weight of the pharmaceutical composition.

Compositions of the invention optionally comprise one or more pharmaceutically acceptable lubricants (including anti-adherents and/or glidants) as excipients. Exemplary lubricants include, but are not limited to, either individually or in combination, glyceryl behapate (e.g., Compritol™ 888 of Gattefosse); stearic acid and salts thereof, including magnesium, calcium and sodium stearates; hydrogenated vegetable oils (e.g., Sterotex™ of Abitec); colloidal silica; talc; waxes; boric acid; sodium benzoate; sodium acetate; sodium fumarate; sodium chloride; DL-leucine; PEG (e.g., Carbowax™ 4000 and Carbowax™ 6000 of the Dow Chemical Company); sodium oleate; sodium lauryl sulfate; and magnesium lauryl sulfate. Such lubricants, if present, may constitute in total about 0.1% to about 10%, about 0.2% to about 8%, or even about 0.25% to about 5%, of the total weight of the pharmaceutical composition.

The composition may, for example, be a pharmaceutical composition (medicament), a foodstuff, food supplement or beverage. The terms "foodstuff", "food supplement", and "beverage" used herein have the normal meanings for those terms, and are not restricted to pharmaceutical preparations. The appropriate pharmaceutical or edible grade of ingredients will be used, according to the desired composition form.

Pharmaceutical compositions according to the present invention include formulations suitable for oral, rectal, intranasal, topical (including transdermal, buccal and sublingual), vaginal, parental (including subcutaneous, intramuscular, intravenous and intradermal) and pulmonary administration. The formulations can conveniently be presented in unit dosage form and can be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with a suitable carrier, such as liquid carriers or finely divided solid carriers or both, and then if necessary shaping the product. Formulations of the subject invention suitable for oral administration can be presented as discrete units such as capsules, cachets or tablets, each containing a predetermined amount of the active ingredient; or as an oil-in-water liquid emulsion, water-in-oil liquid emulsion, or as a supplement within an aqueous solution, for example, a tea. The active ingredient can also be presented as bolus, electuary, or paste.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; mouthwashes comprising the active ingredient in a suitable liquid carrier; and chocolate comprising the active ingredients.

Formulations suitable for topical administration according to the subject invention can be formulated as an ointment, cream, suspension, lotion, powder, solution, paste, gel, spray, aerosol or oil. Alternatively, a formulation can comprise a patch or a dressing such as a bandage or adhesive plaster impregnated with active ingredients, and optionally one or more excipients or diluents. Topical formulations preferably comprise compounds that facilitate absorption of the active ingredients through the skin and into the bloodstream.

Formulations suitable for intranasal administration, wherein the carrier is a solid, include a coarse powder having a particle size, for example, in the range of about 20 to about 500 microns, which is administered in the manner in which snuff is taken, e.g., by rapid inhalation through the nasal passage from a container of the powder held close up to the nose. Suitable formulations wherein the carrier is a liquid for administration by nebulizer, include aqueous or oily solutions of the agent. Formulations may optionally comprise compounds that facilitate absorption of the active ingredients through the skin and into the bloodstream.

Formulations suitable for parenteral administration include aqueous and non-aqueous isotonic sterile injection solutions which can contain antioxidants, buffers, bacteriostats and solutes which render the formulation isotonic with the blood of the intended recipient; and aqueous and non-aqueous sterile suspensions which can include suspending agents and thickening agents, and liposomes or other microparticulate systems which are designed to target the compound to blood components or one or more organs. The formulations can be presented in unit-dose or multi-dose or multi-dose sealed containers, such as for example, ampoules and vials, and can be stored in a freeze-dried (lyophilized) condition requiring only the addition of the sterile liquid carrier, for example, water for injections, immediately prior to use. Extemporaneous injection solutions and suspensions can be prepared from sterile powders, granules and tablets of the kind previously described.

It should be understood that in addition to the ingredients particularly mentioned above, the formulations useful in the present invention can include other agents conventional in the art regarding the type of formulation in question. For example, formulations suitable for oral administration can include such further agents as sweeteners, thickeners, and flavoring agents. It also is intended that the agents, compositions, and methods of this invention be combined with other suitable compositions and therapies.

Various delivery systems are known in the art and can be used to administer a therapeutic agent or composition of the invention, e.g., encapsulation in liposomes, microparticles, microcapsules, receptor-mediated endocytosis and the like. Methods of administration include, but are not limited to, parenteral, intra-arterial, intramuscular, intravenous, intranasal, and oral routes. The pharmaceutical compositions can be provided in the form of tablets, lozenges, granules, capsules, pills, ampoule, suppositories or aerosol form. The pharmaceutical compositions can also be provided in the form of suspensions, solutions, and emulsions of the active ingredient in aqueous or non-aqueous diluents, syrups, granulates or powders.

Pharmaceutical formulations of the invention can be administered simultaneously or sequentially with other drugs or biologically active agents. Examples include, but are not limited to, antioxidants, free radical scavenging agents, peptides, growth factors, antibiotics, bacteriostatic agents, immunosuppressives, anticoagulants, buffering agents, anti-inflammatory agents, anti-pyretics, time-release binders, anesthetics, steroids and corticosteroids.

Preferred unit dosage formulations are those containing a daily dose or unit, daily subdose, or an appropriate fraction thereof, of an agent. Therapeutic amounts can be empirically determined and will vary with the condition being treated, the subject being treated, and the efficacy and toxicity of the agent. Similarly, suitable dosage formulations and methods of administering the agents can be readily determined by those of ordinary skill in the art.

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

LBEPRO

1:1 Cocrystal of Lithium Benzoate and L-Proline

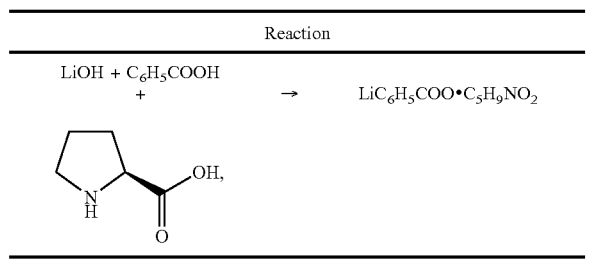

Lithium hydroxide (>98%, anhydrous, used as received from Sigma Aldrich, 47.9 mg, 2.0 mmol), benzoic acid (>99% used as received from Sigma Aldrich, 244.2 mg, 2.0 mmol) and L-proline (99+% pure, used as received from Aldrich, 230.2 mg, 2.0 mmol)) were dissolved in 2.0 mL of deionized water. The solution was evaporated on a hot plate until crystals emerged from solution. Colorless plates (150.5 mg) were collected from the hot solution.

Crystals of LBEPRO were characterized by single crystal x-ray crystallography (Table 1) and powder x-ray diffraction (Bruker D8 advance, Cu radiation) (FIG. 1; calculated (top) and experimental (bottom)). As can be seen from FIG. 1, major peaks lie at about the following positions: 7.5, 11.6, 16.7, 19.4, 20.4, 20.9, 22.6, 23.2 and 24.7.

Figure 2:
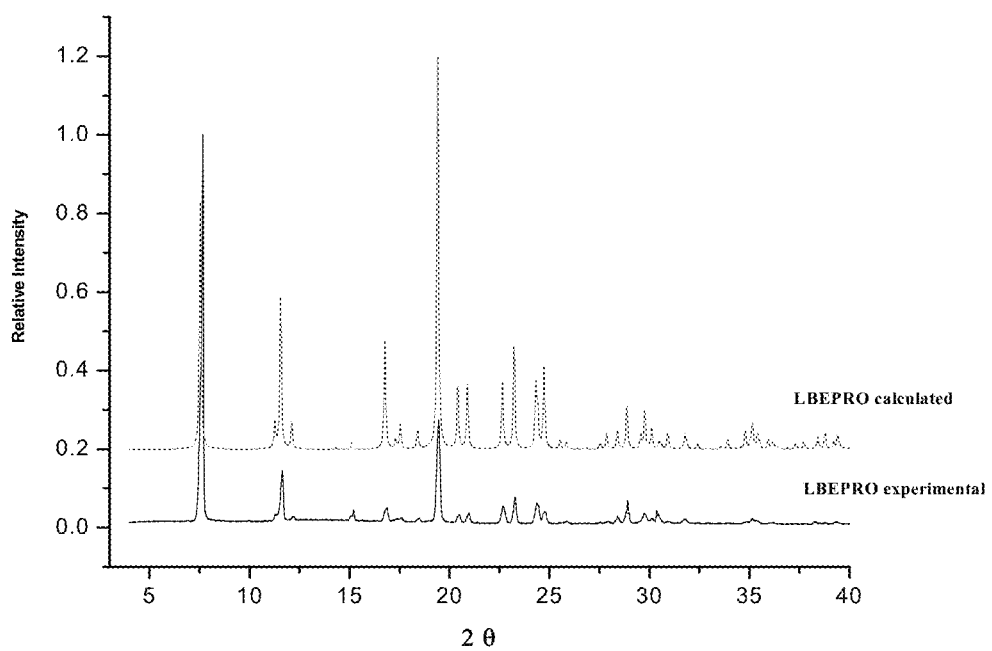
FIG. 2 is a comparison of the calculated and experimental powder x-ray diffraction patterns of LBEPRO, as described further in Example 1.

FIG. 2 shows a comparison of the experimental and calculated powder x-ray diffraction patterns of LBEPRO.

Figure 3:
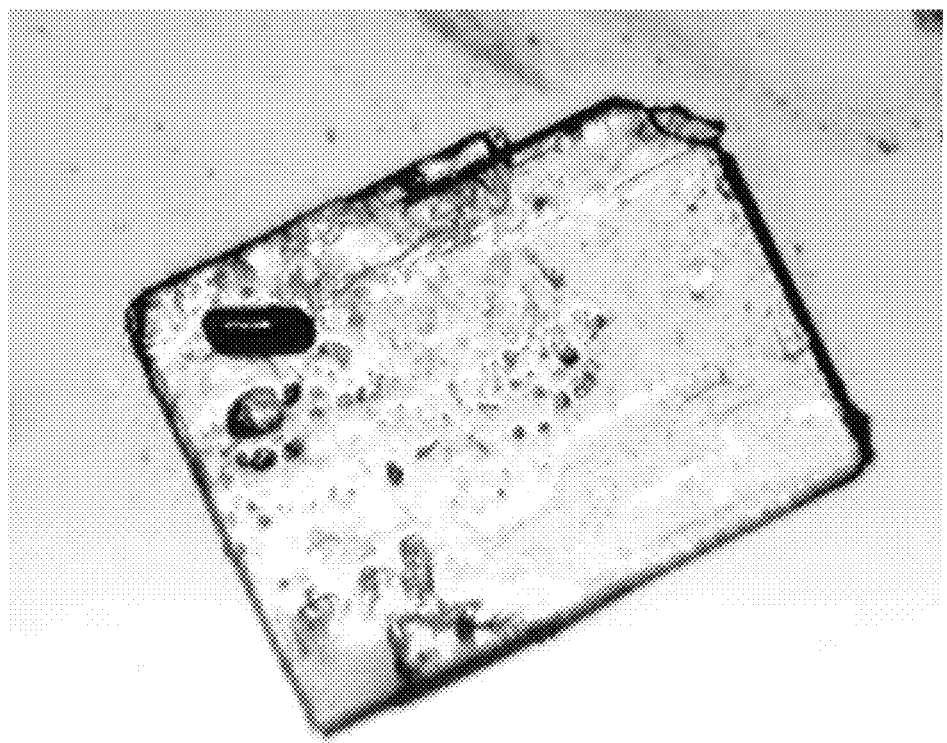
FIG. 3 is a digital microscope image of LBEPRO, as described further in Example 1.

FIG. 3 shows a digital microscope image of LBEPRO crystals.

The single crystal x-ray structure reveals that LBEPRO is a 1:1 cocrystal of lithium benzoate and L-proline. There are four benzoates, four L-prolines and four lithium cations in the unit cell. Each lithium cation is bridged by four carboxylate moieties (from two L-prolines and two benzoate anions) to form square grids.

Figure 4:
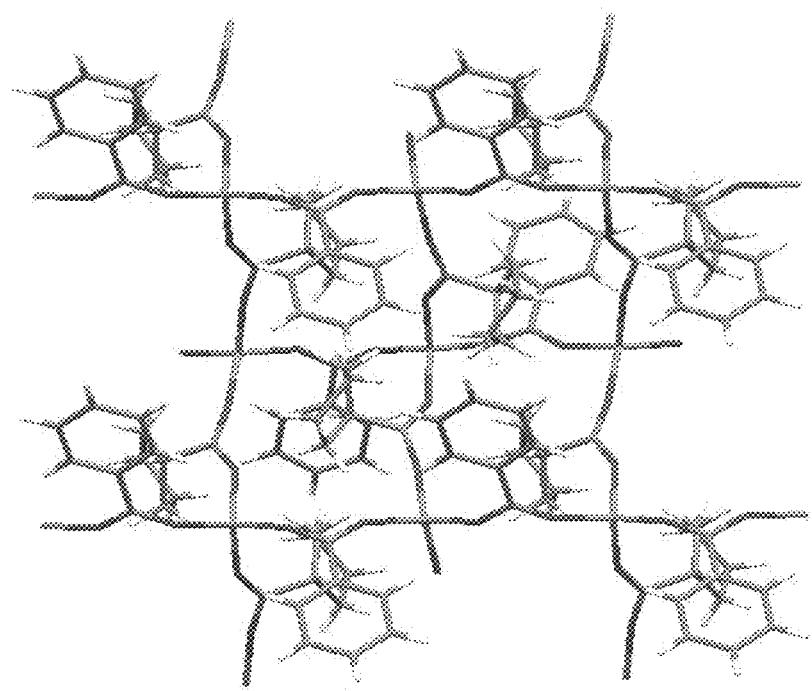
FIG. 4 is a crystal packing diagram of LBEPRO, as described further in Example 1.

FIG. 4 shows the crystal packing diagram of LBEPRO.

TABLE 1

Single crystal X-ray diffraction data for LBEPRO (Bruker-AXS APEX2 CCD diffractometer)

Crystallographic data

| | | |
|---|---|---|
| Empirical formula | $C_{12}H_{14}LiNO_4$ | |
| Formula weight | 243.18 | |
| Temperature | 228 (2) K | |
| Wavelength | 1.54178 Å | |
| Crystal system | Orthorhombic | |
| Space group | $P2_12_12_1$ | |
| Unit cell dimensions | a = 10.1024 (2) Å | $\alpha = 90°$ |
| | b = 10.5639 (2) Å | $\beta = 90°$ |
| | c = 11.7158 (2) Å | $\gamma = 90°$ |
| Volume | 1250.32 (4) Å$^3$ | |
| Z | 4 | |
| Density (calculated) | 1.292 Mg/m$^3$ | |
| Reflections collected | 11172 | |

TABLE 1-continued

Single crystal X-ray diffraction data for LBEPRO
(Bruker-AXS APEX2 CCD diffractometer)

| | |
|---|---|
| Independent reflections | 2250 [R(int) = 0.0393] |
| Final R indices [I > 2sigma(I)] | R1 = 0.0329, wR2 = 0.0824 |
| R indices (all data) | R1 = 0.0343, wR2 = 0.0835 |

Example 2

LIS4HPR

1:1 Cocrystal of Lithium Salicylate and 4-Hydroxy Proline

Reaction

LiOH + $C_7H_6O_3$ + → $C_7H_5O_3LiC_5H_9NO_3$

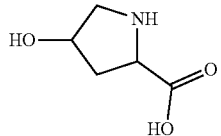

Lithium hydroxide (>98%, anhydrous, used as received from Sigma Aldrich, 23.9 mg, 1.0 mmol), salicylic acid (>99% used as received from Sigma Acros Organics, 138.1 mg, 1.0 mmol) and 4-hydroxy proline (99+% pure, used as received from Aldrich, 131.1 mg, 1.0 mmol)) were dissolved in 3.0 mL of deionised water. The solution was evaporated on a hot plate until crystals emerged from solution. Colorless plates (226.0 mg) were collected from the hot solution.

Figure 5:
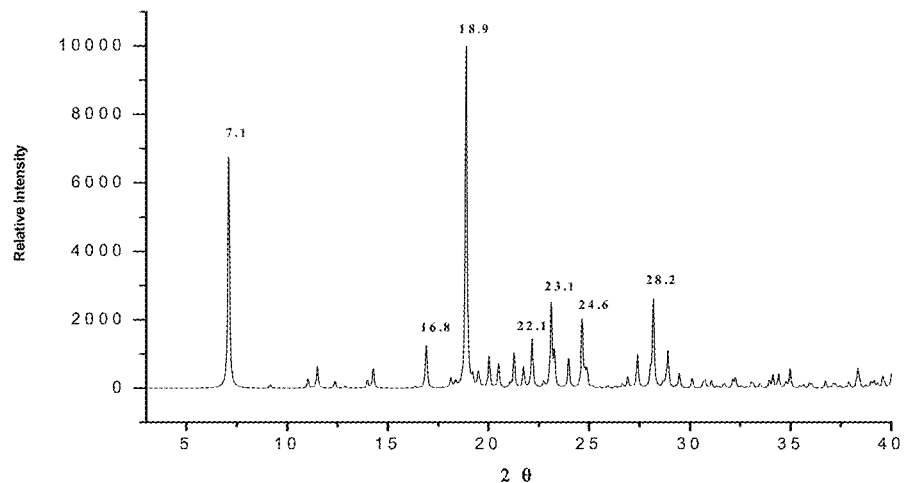
FIG. 5 the calculated and experimental powder x-ray diffraction pattern of LIS4HPR, as described further in Example 2.
Figure 5:
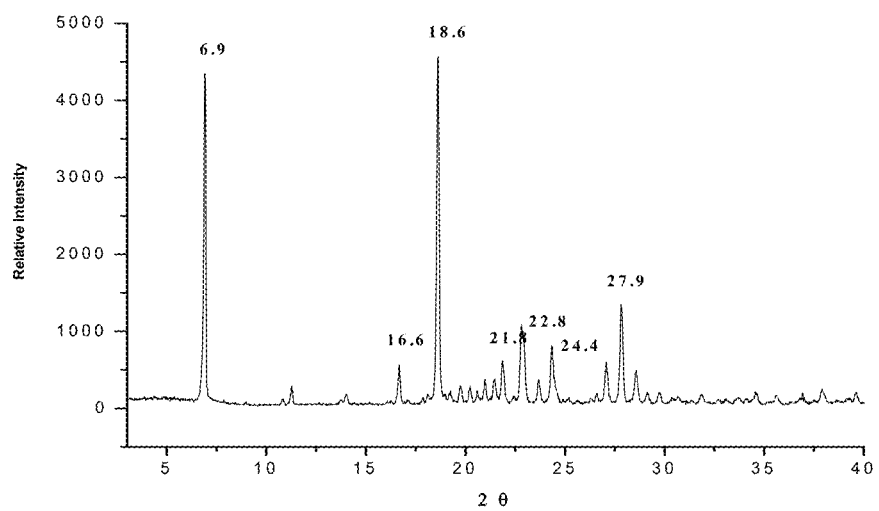

Crystals of LIS4HPR were characterized by single crystal x-ray crystallography (Table 2) and powder x-ray diffraction (Bruker D8 advance, Cu radiation) (FIG. 5; calculated (top) and experimental (bottom)). As can be seen from FIG. 5, major peaks lie at about the following positions: 6.9, 16.6, 18.6, 21.8, 22.8, 24.4 and 27.9.

Figure 6:
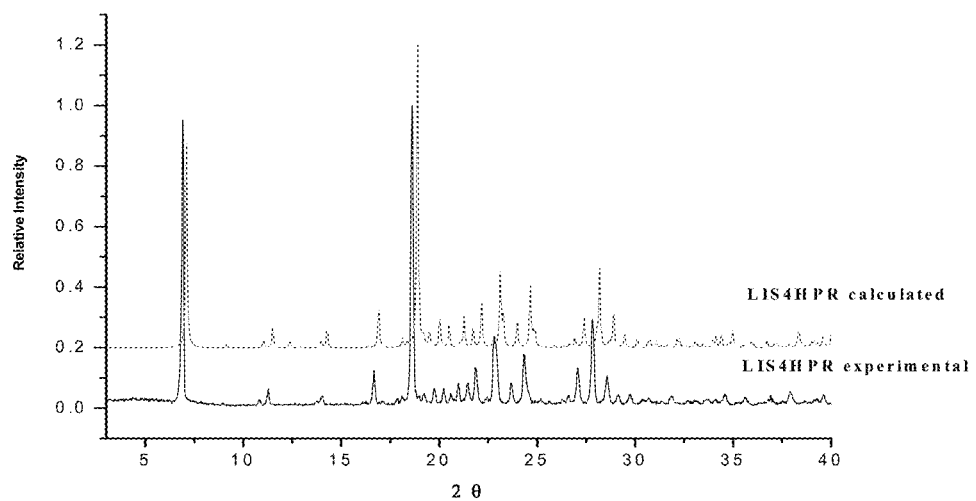
FIG. 6 is a comparison of the calculated and experimental powder x-ray diffraction patterns of LIS4HPR, as described further in Example 2.

FIG. 6 shows a comparison of the experimental and calculated powder x-ray diffraction patterns of LIS4HPR.

Figure 7:
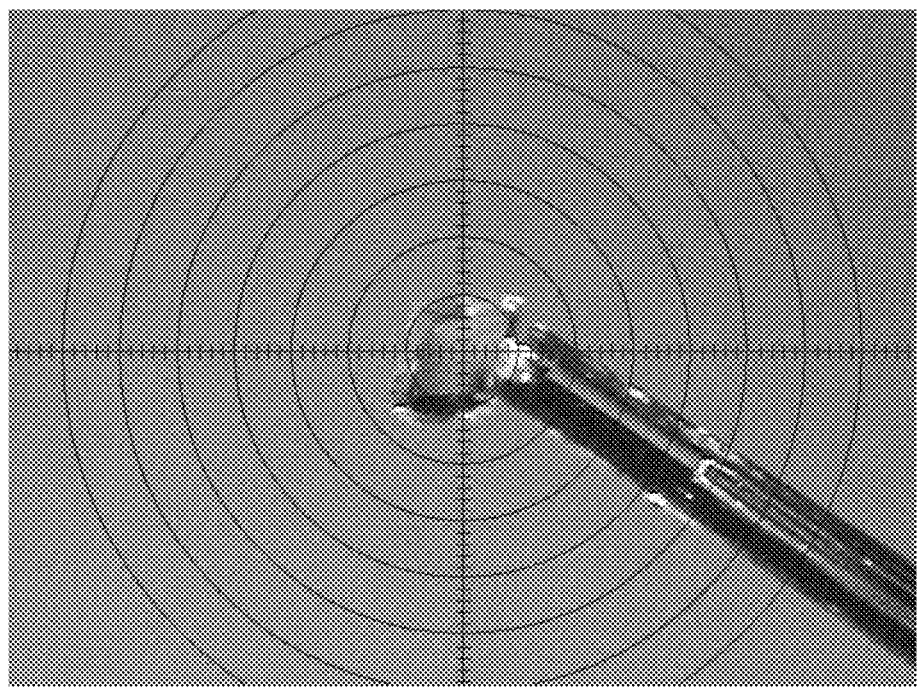
FIG. 7 is a digital microscope image of LIS4HPR, as described further in Example 2.

FIG. 7 shows a digital microscope image of LIS4HPR crystals.

The single crystal x-ray structure reveals that LIS4HPR is a 1:1 cocrystal of lithium salicylate and 4-hydroxy proline. Each unit cell contains eight salicylate anions, eight hydroxy prolines and eight lithium cations. Each lithium cation is bridged by four carboxylate moieties (two 4-hydroxy prolines and two salicylate anions) to form square grids.

Figure 8:
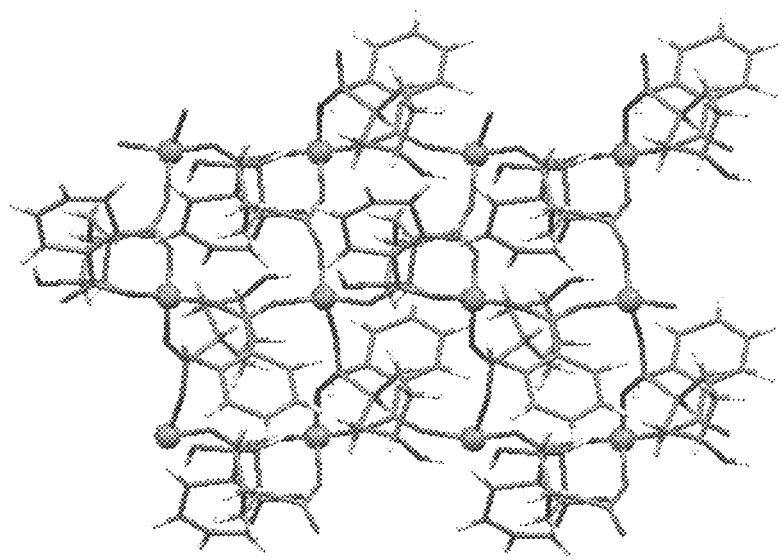
FIG. 8 is a crystal packing diagram of LIS4HPR, as described further in Example 2.

FIG. 8 shows the crystal packing diagram of LIS4HPR.

TABLE 2

Single crystal X-ray diffraction data for LIS4HPR
(Bruker-D8 venture photon diffractometer)

| Crystallographic data | |
|---|---|
| Empirical formula | $C_{12}H_{14}LiNO_6$ |
| Formula weight | 275.18 |
| Temperature | 100 (2) K |
| Wavelength | 1.54178 Å |
| Crystal system | Orthorhombic |
| Space group | $P2_12_12_1$ |

TABLE 2-continued

Single crystal X-ray diffraction data for LIS4HPR
(Bruker-D8 venture photon diffractometer)

| | | |
|---|---|---|
| Unit cell dimensions | a = 9.7805 (5) Å | α = 90° |
| | b = 10.4758 (5) Å | β = 90° |
| | c = 24.8959 (12) Å | γ = 90° |
| Volume | 2250.8 (2) Å³ | |
| Z | 8 | |
| Density (calculated) | 1.433 Mg/m³ | |
| Reflections collected | 40970 | |
| Independent reflections | 4351 [R(int) = 0.0546] | |
| Final R indices [I > 2sigma(I)] | R1 = 0.0385, wR2 = 0.0809 | |
| R indices (all data) | R1 = 0.0455, wR2 = 0.0839 | |

Example 3

LISBAL

1:1 Cocrystal of Lithium Salicylate and Beta Alanine

Reaction

LiOH + $C_7H_6O_3$ + → $LiC_7H_5O_3 \cdot C_3H_7NO_2$

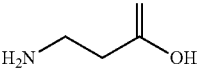

Lithium hydroxide (>98%, anhydrous, used as received from Sigma Aldrich, 23.9 mg, 1.0 mmol), Salicylic acid (>99% used as received from Sigma Acros Organics, 138.1 mg, 1.0 mmol) and beta alanine (99+% pure, used as received from Aldrich, 178.1 mg, 2.0 mmol)) were dissolved in 5.0 mL of deionised water. The solution was evaporated on a hot plate until crystals emerged from solution. Colorless plates (85.0 mg) were collected from the hot solution.

Figure 9:
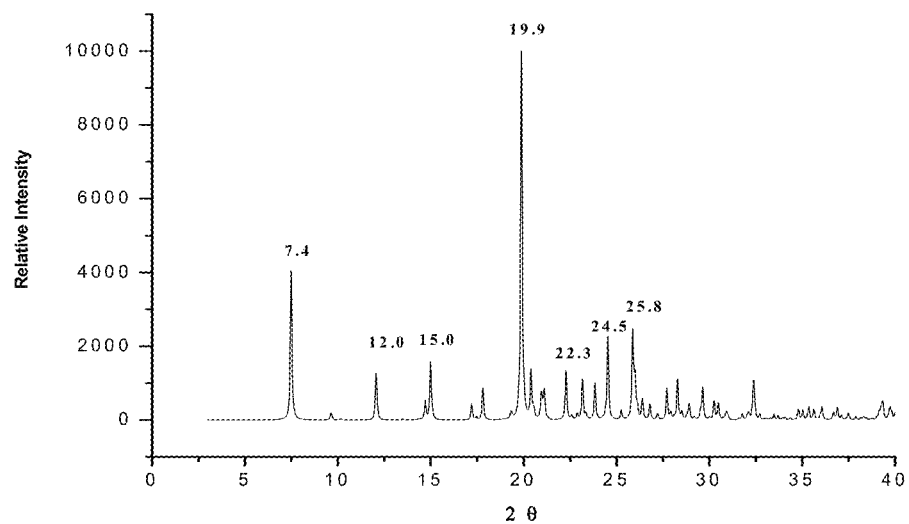
FIG. 9 is the calculated and experimental powder x-ray diffraction pattern of LISBAL, as described further in Example 3.
Figure 9:
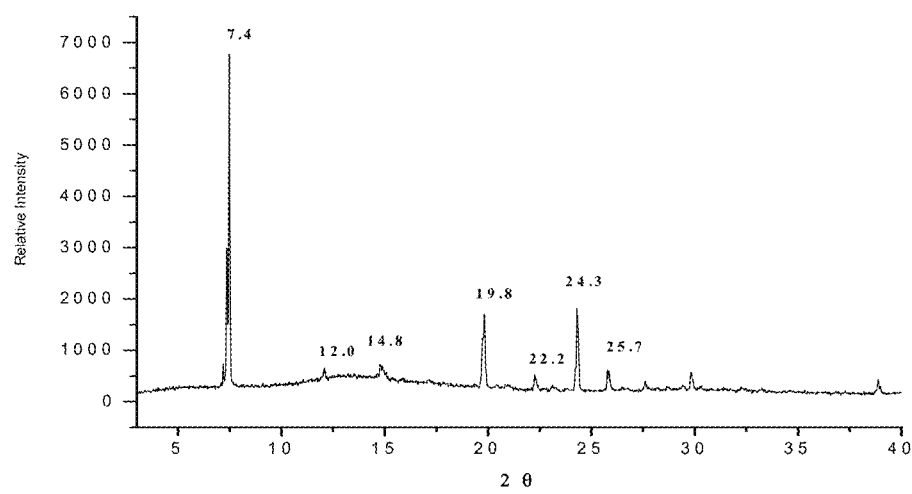

Crystals of LISBAL were characterized by single crystal x-ray crystallography (Table 3) and powder x-ray diffraction (Bricker D8 advance, Cu radiation) (FIG. 9; calculated (top) and experimental (bottom)). As can be seen from FIG. 9, major peaks lie at about the following positions: 7.4, 12.0, 15.0, 19.8, 22.3, 24.5 and 25.8.

Figure 10:
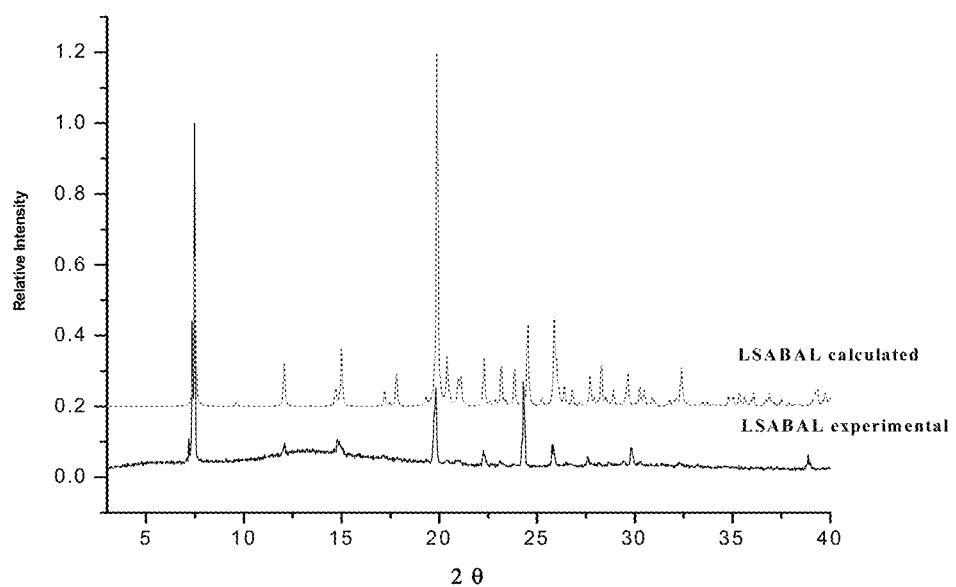
FIG. 10 is a comparison of the calculated and experimental powder x-ray diffraction patterns of LISBAL, as described further in Example 3.

FIG. 10 shows a comparison of experimental and calculated powder x-ray diffraction patterns of LISBAL.

Figure 11:
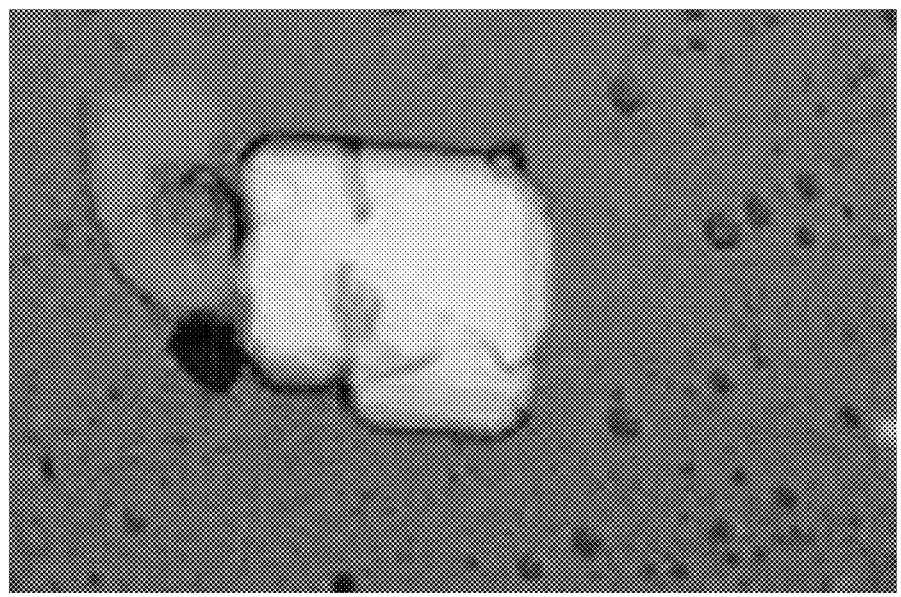
FIG. 11 is a digital microscope image of LISBAL, as described further in Example 3.

FIG. 11 shows a digital microscope image of LISBAL crystals.

The single crystal x-ray structure reveals that LISBAL is a 1:1 cocrystal of lithium salicylate and beta alanine. Each lithium cation is bridged by four carboxylate moieties, two from beta alanine (Li—O bond distances: 1.920 Å, 1.923 Å) and two from salicylate anions (Li—O bond distances: 1.921 Å, 1.939 Å) to form a square grid.

Figure 12:
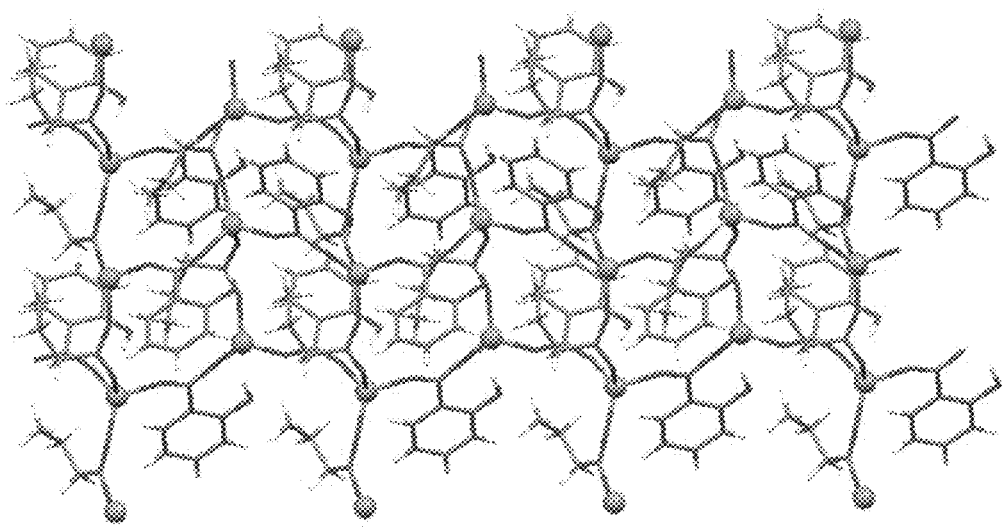
FIG. 12 is a crystal packing diagram of LISBAL, as described further in Example 3.

FIG. 12 shows the crystal packing diagram of LISBAL.

TABLE 3

Single crystal X-ray diffraction data for LISBAL
(Bruker-D8 venture photon diffractometer)

| Crystallographic data | |
|---|---|
| Empirical formula | $C_{20}H_{24}Li_2N_2O_{10}$ |
| Formula weight | 466.29 |
| Temperature | 120 (2) K |

TABLE 3-continued

Single crystal X-ray diffraction data for LISBAL
(Bruker-D8 venture photon diffractometer)

| | |
|---|---|
| Wavelength | 1.54178 Å |
| Crystal system | Orthorhombic |
| Space group | $P2_12_12_1$ |
| Unit cell dimensions | a = 9.3574 (6) Å    α = 90° |
| | b = 9.9529 (6) Å    β = 90° |
| | c = 23.5985 (15) Å   γ = 90° |
| Volume | 2197.8 (2) Å$^3$ |
| Z | 4 |
| Density (calculated) | 1.409 Mg/m$^3$ |
| Reflections collected | 30531 |
| Independent reflections | 3692 [R(int) = 0.0543] |
| Final R indices [I > 2sigma(I)] | R1 = 0.0261, wR2 = 0.0607 |
| R indices (all data) | R1 = 0.0286, wR2 = 0.0620 |

Example 4

LOXBAL.H$_2$O

Monohydrate of the 1:2 Cocrystal of Lithium Oxalate and Beta Alanine

---
Reaction

2LiOH + C$_2$H$_2$O$_4$
+                    →    C$_2$O$_4$Li$_2$(H$_2$O)(C$_3$H$_7$NO$_2$)$_2$

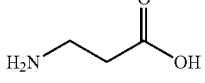

---

Lithium hydroxide (>98%, anhydrous, used as received from sigma aldrich, 47.9 mg, 2.0 mmol), oxalic acid (>99% used as received from Sigma Aldrich, 90.0 mg, 1.0 mmol) and beta alanine (99+% pure, used as received from Aldrich, 178.1 mg, 2.0 mmol)) were dissolved in 3.0 mL of deionised water. The solution was evaporated on a hot plate until crystals emerged from solution. Colorless needles (140.0 mg) were collected from the hot solution.

Crystals of LOXBAL.H$_2$O were characterized by single crystal x-ray crystallography (Table 4).

Figure 13:
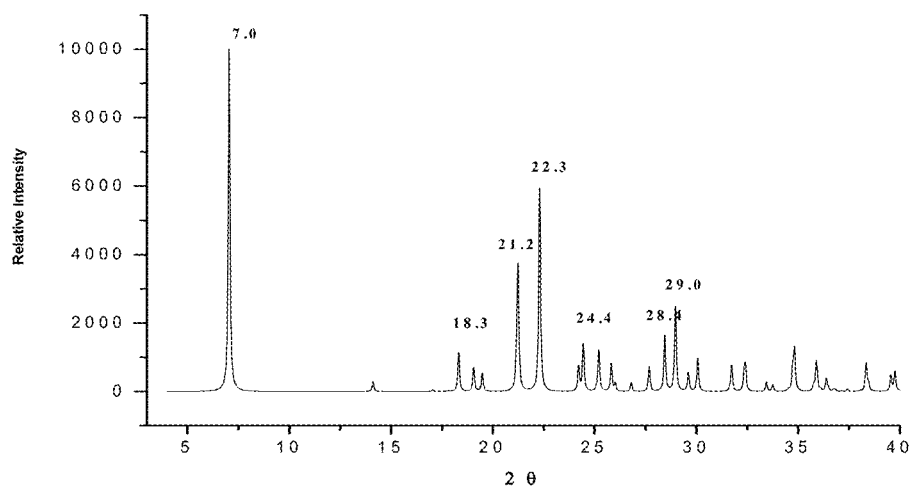
FIG. 13 is the calculated x-ray diffraction pattern of LOXBAL.H$_2$O, as described further in Example 4.

FIG. 13 shows the calculated x-ray diffraction patterns of LOXBAL.H$_2$O. As can be seen from FIG. 13, major peaks were observed in the calculated powder x-ray diffraction pattern at approximately the following positions: 7.0, 18.3, 21.2, 22.3, 24.4, 28.4 and 29.0.

Figure 14:
FIG. 14 is a digital microscope image of LOXBAL.H$_2$O, as described further in Example 4.

FIG. 14 shows a digital microscope image of LOXBAL.H$_2$O crystals.

The single crystal x-ray structure reveals that LOXBAL.H$_2$O is a 1:2 ionic cocrystal of lithium oxalate and beta alanine with one water molecule in the crystal lattice. Each lithium cation is coordinated to three oxalate bridging carboxylates, one carboxylate of beta alanine and a water molecule that is coordinated as an aqua ligand. The resulting structure is that of a 2 dimensional network (FIG. 15) that is further connected through hydrogen bonds of water molecules to form a three dimensional hydrogen-bonded network.

Figure 15:
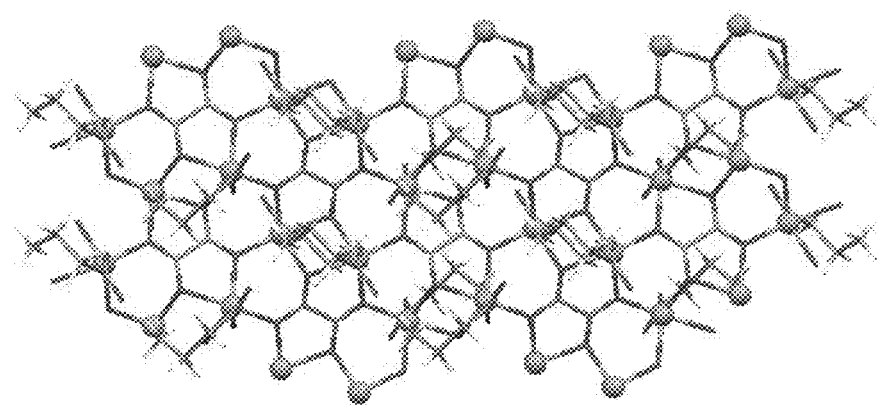
FIG. 15 is a crystal packing diagram of LOXBAL.H$_2$O, as described further in Example 4.

FIG. 15 shows the crystal packing diagram of LOXBAL.H$_2$O.

TABLE 4

Single crystal X-ray diffraction data for LOXBAL · H2O
(Bruker-D8 venture photon diffractometer)

| Crystallographic data | |
|---|---|
| Empirical formula | C$_8$H$_{16}$Li$_2$N$_2$O$_9$ |
| Formula weight | 149.05 |
| Temperature | 100 (2) K |
| Wavelength | 1.54178 Å |
| Crystal system | Monoclinic |
| Space group | C2/c |
| Unit cell dimensions | a = 25.2895 (15) Å   α = 90° |
| | b = 5.3066 (3) Å     β = 97.360(2)° |
| | c = 10.0243 (6) Å    γ = 90° |
| Volume | 1334.19 (14) Å$^3$ |
| Z | 4 |
| Density (calculated) | 1.484 Mg/m$^3$ |
| Reflections collected | 9904 |
| Independent reflections | 1106 [R(int) = 0.0455] |
| Final R indices [I > 2sigma(I)] | R1 = 0.0307, wR2 = 0.0777 |
| R indices (all data) | R1 = 0.0325, wR2 = 0.0799 |

Example 5

LSCBTN.2H$_2$O

The Dihydrate of the 1:1 Cocrystal of Lithium Saccharinate and Betaine

---
Reaction

LiOH + C$_7$H$_5$NO$_3$S
+                    →    C$_7$H$_4$SO$_3$NLi(H$_2$O)$_2$•C$_5$H$_{11}$NO$_2$

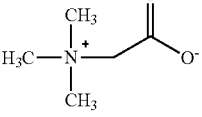

---

Lithium hydroxide (>98%, anhydrous, used as received from Sigma Aldrich, 23.9 mg, 1.0 mmol), saccharin (>99% used as received from Sigma Aldrich, 183.1 mg, 1.0 mmol) and betaine (99+% pure, used as received from Aldrich, 117.1 mg, 1.0 mmol) were dissolved in 4.0 mL of deionised water. The solution was evaporated on a hot plate until crystals emerged from solution. Colorless plates (127.0 mg) were collected from the hot solution.

Figure 16:
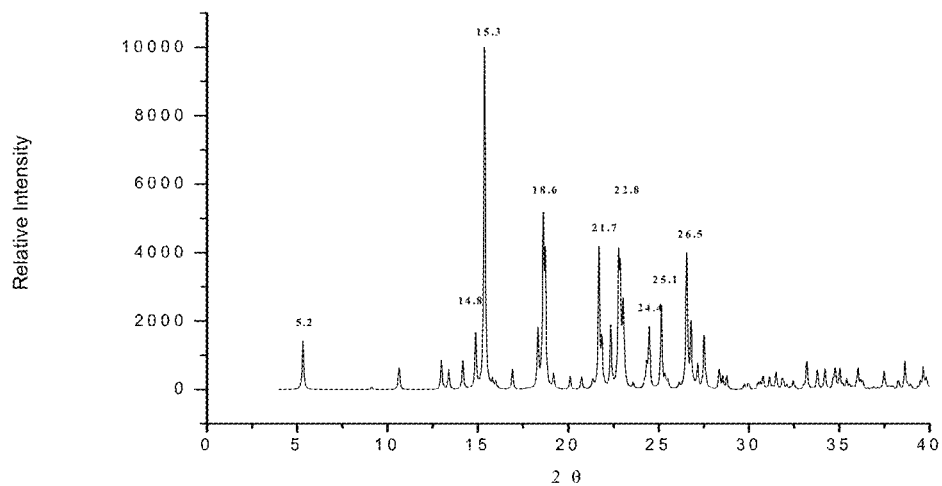
FIG. 16 is the calculated and experimental powder x-ray diffraction pattern of LSCBTN.2H$_2$O, as described further in Example 5.
Figure 16:
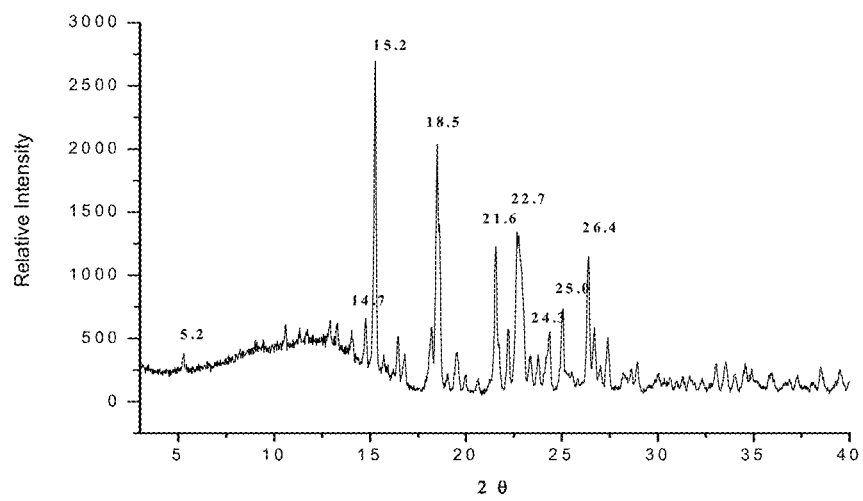

Crystals of LSCBTN.2H$_2$O were characterized by single crystal x-ray crystallography (Table 5) and powder x-ray diffraction (Brucker D8 advance, Cu radiation) (FIG. 16; calculated (top) and experimental (bottom)). As can be seen from FIG. 16, major peaks lie at about the following positions: 5.2, 14.7, 15.2, 18.5, 21.6, 22.7, 24.3, 25.0 and 26.4.

Figure 17:
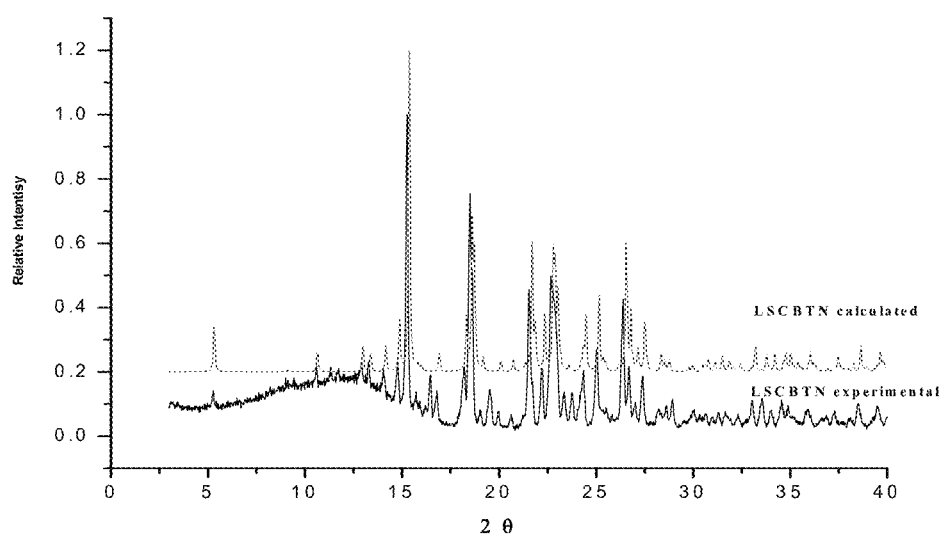
FIG. 17 is a comparison of the calculated and experimental powder x-ray diffraction patterns of LSCBTN.2H$_2$O, as described further in Example 5.

FIG. 17 shows a comparison of the experimental and calculated powder x-ray diffraction patterns of LSCBTN.2H$_2$O.

Figure 18:
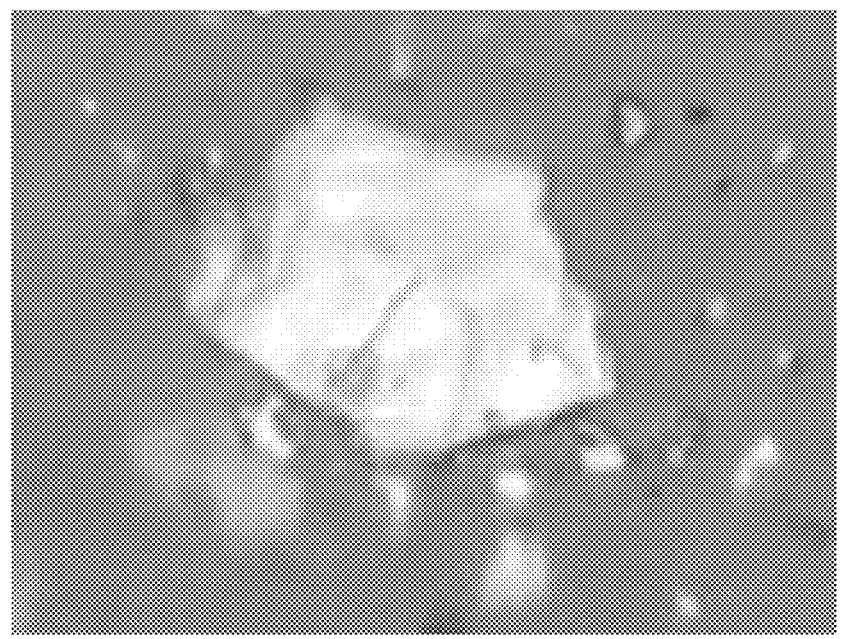
FIG. 18 is a digital microscope image of LSCBTN.2H$_2$O crystals, as described further in Example 5.

FIG. 18 shows a digital microscope image of LSCBTN.2H$_2$O crystals.

The single crystal x-ray structure reveals that LSCBTN.2H$_2$O is a 1:1 cocrystal of lithium saccharinate and betaine with two water molecules in the crystal lattice. Each lithium cation is bridged by two carboxylate moieties of betaine (Li—O bond distances: 1.921 Å, 1.940 Å) to form a liner chain and is also coordinated by two water molecules (Li—O bond distances: 1.955 Å and 1.893 Å). These water molecules form hydrogen bonds with the carbonyl and basic nitrogen of saccharinate anions.

Figure 19:
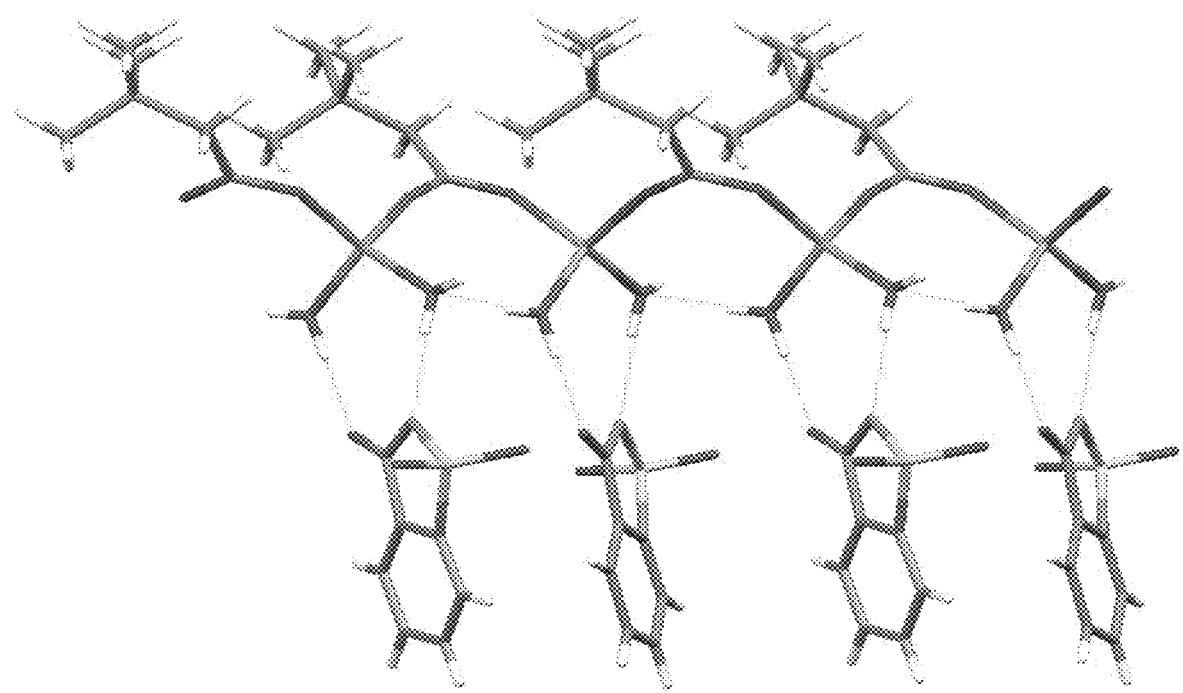
FIG. 19 is a crystal packing diagram of LSCBTN.2H$_2$O, as described further in Example 5.

FIG. 19 shows the crystal packing diagram of LSCBTN.2H$_2$O.

TABLE 5

Single crystal X-ray diffraction data for LSCBTN.2H$_2$O
(Bruker-AXS APEX2 CCD diffractometer)

Crystallographic data

| | |
|---|---|
| Empirical formula | C$_{12}$H$_{19}$LiN$_2$O$_7$S |
| Formula weight | 342.29 |
| Temperature | 296 (2) K |
| Wavelength | 1.54178 Å |
| Crystal system | Orthorhombic |
| Space group | P b c a |
| Unit cell dimensions | a = 11.9004 (2) Å   α = 90° |
| | b = 8.1845 (10) Å   β = 90° |
| | c = 33.2368 (15) Å   γ = 90° |
| Volume | 3237.22 (8) Å$^3$ |
| Z | 8 |
| Density (calculated) | 1.405 Mg/m$^3$ |
| Reflections collected | 26918 |
| Independent reflections | 2941 [R(int) = 0.0524] |
| Final R indices [I > 2sigma(I)] | R1 = 0.0358, wR2 = 0.0925 |
| R indices (all data) | R1 = 0.0440, wR2 = 0.0978 |

Example 6

LSCSAR

Monohydrate of 1:1 Cocrystal of Lithium Saccharinate and Sarcosine

Reaction

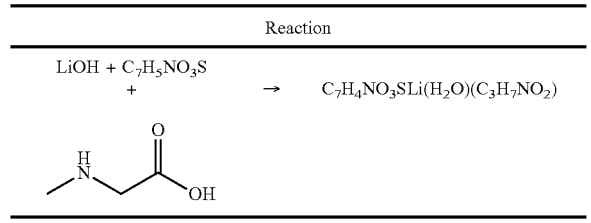

LiOH + C$_7$H$_5$NO$_3$S + [sarcosine] → C$_7$H$_4$NO$_3$SLi(H$_2$O)(C$_3$H$_7$NO$_2$)

Lithium hydroxide (>98%, anhydrous, used as received from Sigma Aldrich, 23.9 mg, 1.0 mmol), saccharin (>99% used as received from Sigma Aldrich, 183.1 mg, 1.0 mmol) and sarcosine (99+% pure, used as received from Aldrich, 178.1 mg, 2.0 mmol) were dissolved in 4.0 mL of deionised water. The solution was evaporated on a hot plate until crystals emerged from solution. Colorless needles (190.0 mg) were collected from the hot solution.

Figure 20:
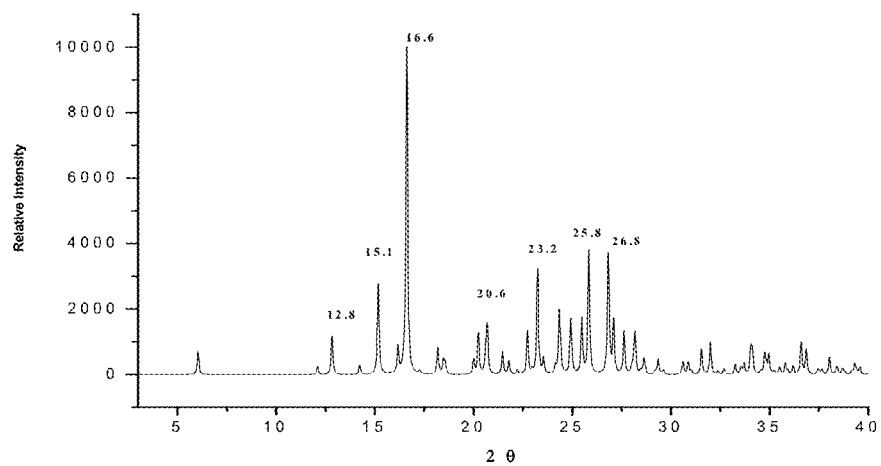
FIG. 20 is the calculated and experimental powder x-ray diffraction patterns of LSCSAR, as described further in Example 6.
Figure 20:
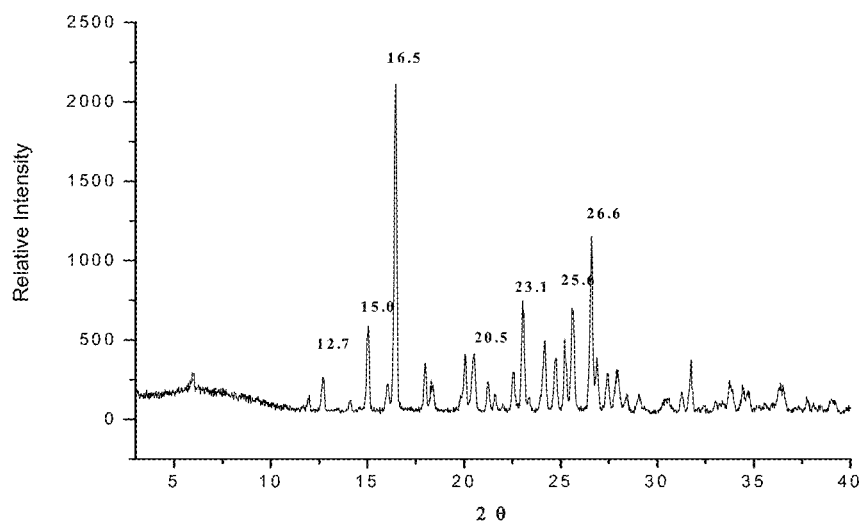

Crystals of LSCSAR were characterized by single crystal x-ray crystallography (Table 6) and powder x-ray diffraction (Bruker D8 advance, Cu radiation) (FIG. 20; calculated (top) and experimental (bottom)). As can be seen from FIG. 20, major peaks lie at about the following positions: 12.7, 15.0, 16.5, 20.5, 23.1, 25.6 and 26.6.

Figure 21:
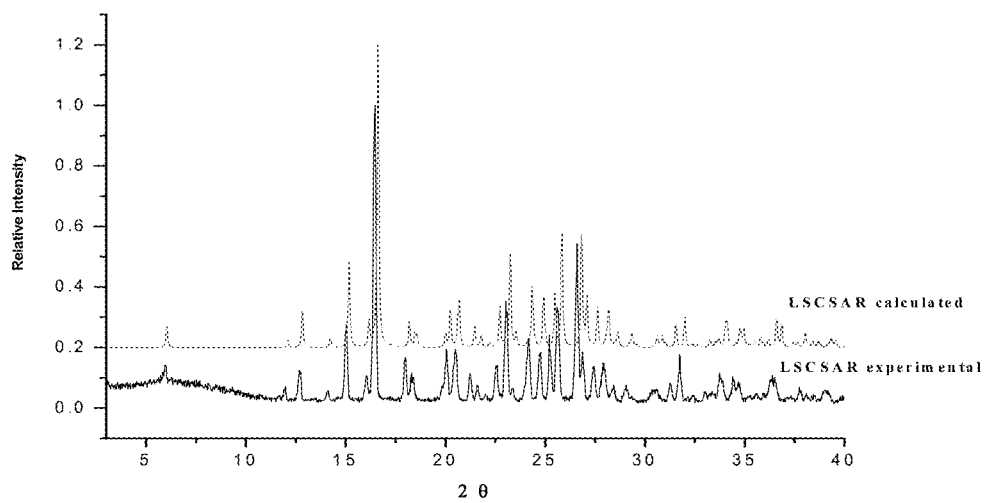
FIG. 21 is a comparison of the experimental and calculated powder x-ray diffraction patterns of LSCSAR, as described further in Example 6.

FIG. 21 shows a comparison of the experimental and calculated powder x-ray diffraction patterns of LSCSAR.

Figure 22:
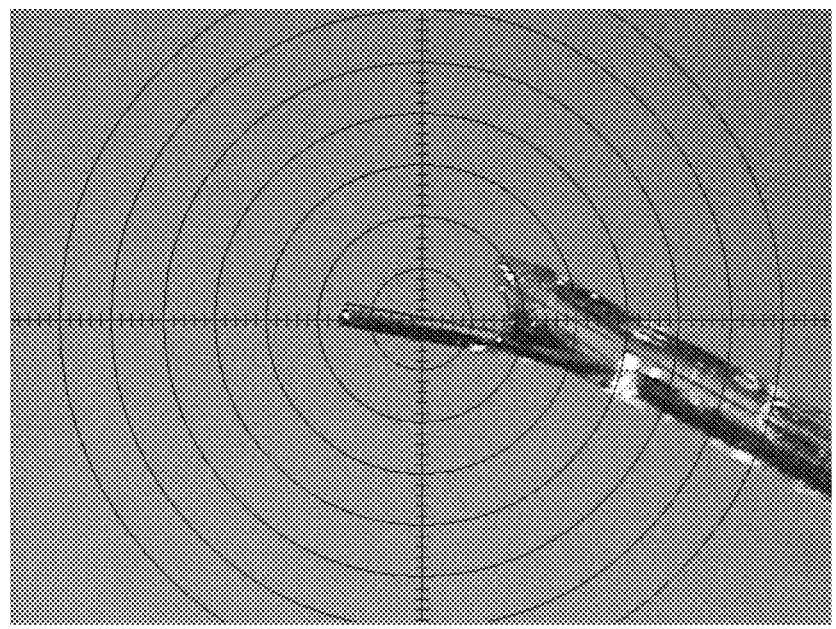
FIG. 22 is a digital microscope image of LSCSAR crystals, as described further in Example 6.

FIG. 22 shows a digital microscope image of LSCSAR crystals.

The single crystal x-ray structure reveals that LSCSAR is a 1:1 cocrystal of lithium saccharinate and sarcosine with one water molecule coordinated to lithium as an aqua ligand. Each lithium cation is coordinated by two carboxylates of sarcosine, one carbonyl functional group of saccharinate and one water molecule to achieve distorted tetrahedral coordination. Lithium cations are bridged by carboxylate moieties of sarcosine to form linear chains and the aqua ligands form hydrogen bonds to adjacent chains via the basic nitrogen atom of saccharinate.

Figure 23:
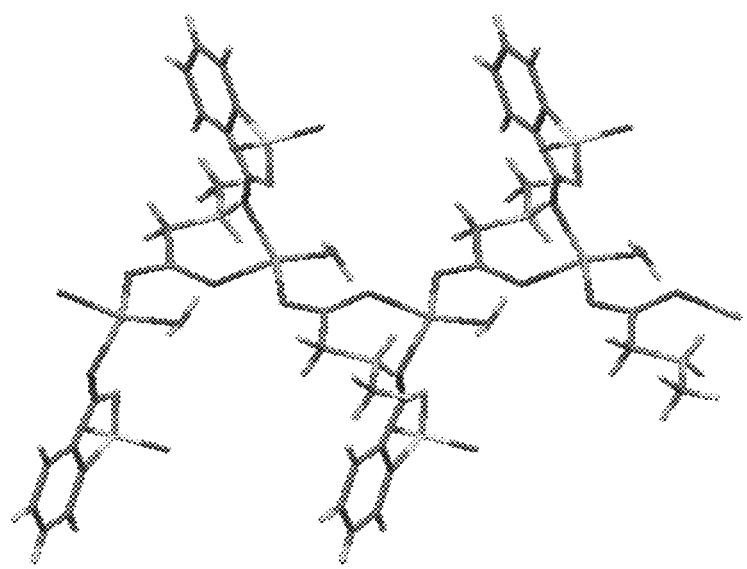
FIG. 23 is a crystal packing diagram of LSCSAR, as described further in Example 6.

FIG. 23 shows the crystal packing diagram of LSCSAR.

TABLE 6

Single crystal X-ray diffraction data for LSCSAR
(Bruker-D8 venture photon diffractometer)

Crystallographic data

| | |
|---|---|
| Empirical formula | C$_{10}$H$_{13}$LiN$_2$O$_6$S |
| Formula weight | 296.22 |
| Temperature | 111 (2) K |
| Wavelength | 1.54178 Å |
| Crystal system | Orthorhombic |
| Space group | Pbca |
| Unit cell dimensions | a = 7.8188 (2) Å   α = 90° |
| | b = 10.9548 (3) Å   β = 90° |
| | c = 29.2415 (7) Å   γ = 90° |
| Volume | 2504.63 (11) Å$^3$ |
| Z | 8 |
| Density (calculated) | 1.571 Mg/m$^3$ |
| Reflections collected | 12748 |
| Independent reflections | 2180 [R(int) = 0.1089] |
| Final R indices [I > 2sigma(I)] | R1 = 0.0399, wR2 = 0.0863 |
| R indices (all data) | R1 = 0.0536, wR2 = 0.0910 |

Example 7

LISPRO

1:1 Cocrystal of Lithium Salicylate and L-Proline

Reaction

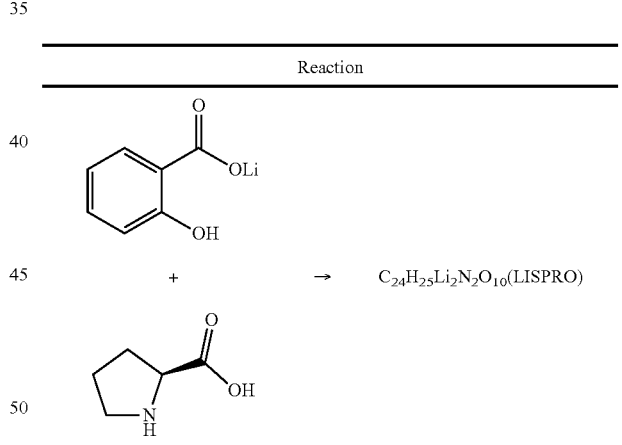

+ → C$_{24}$H$_{25}$Li$_2$N$_2$O$_{10}$(LISPRO)

Lithium Salicylate (99+%, anhydrous, used as received from Sigma Aldrich, 1 mmol) and L-proline (99+% pure, used as received from Sigma Aldrich, 1 mmol) were dissolved in 2.0 ml of hot deionised water. It was maintained on the hot plate (75-90° C.) until crystal formation. Colorless crystals (approximately 218 mg) were collected.

Figure 24:
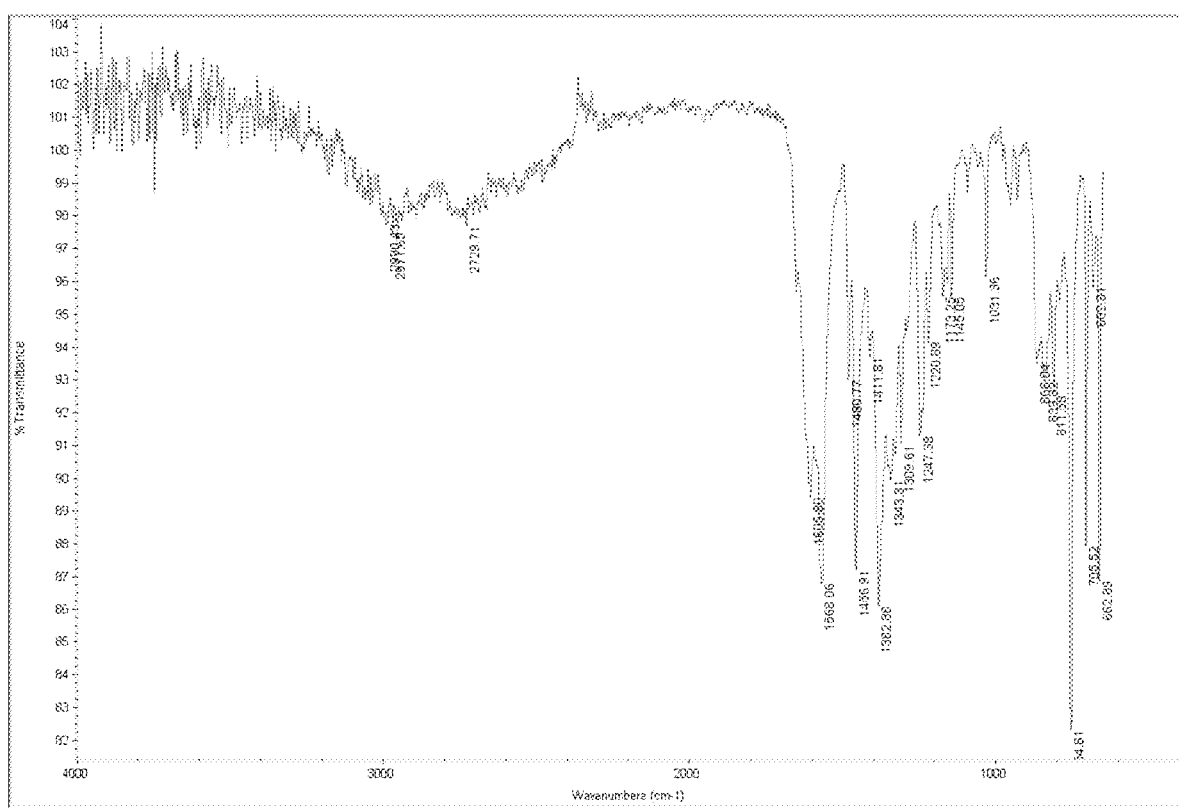
FIG. 24 is a FT-IR diagram of LISPRO, as described further in Example 7.
Figure 25:
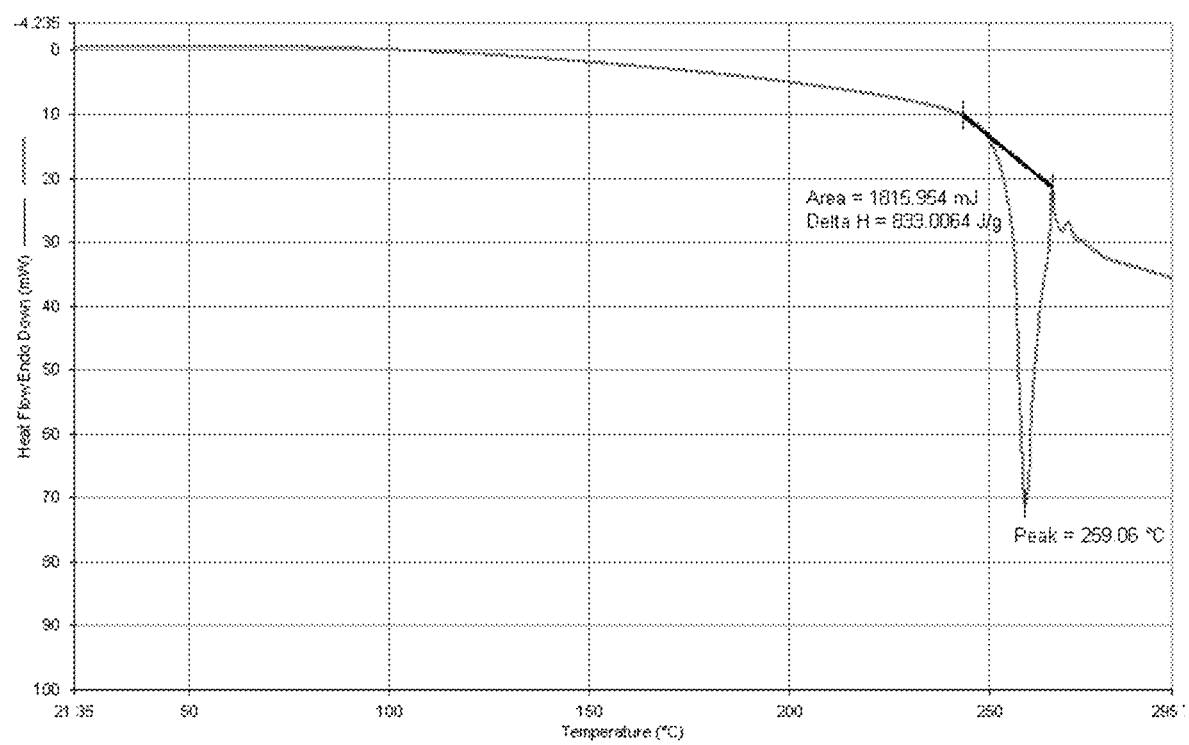
FIG. 25 is a DSC diagram of LISPRO, as described further in Example 7.
Figure 26:
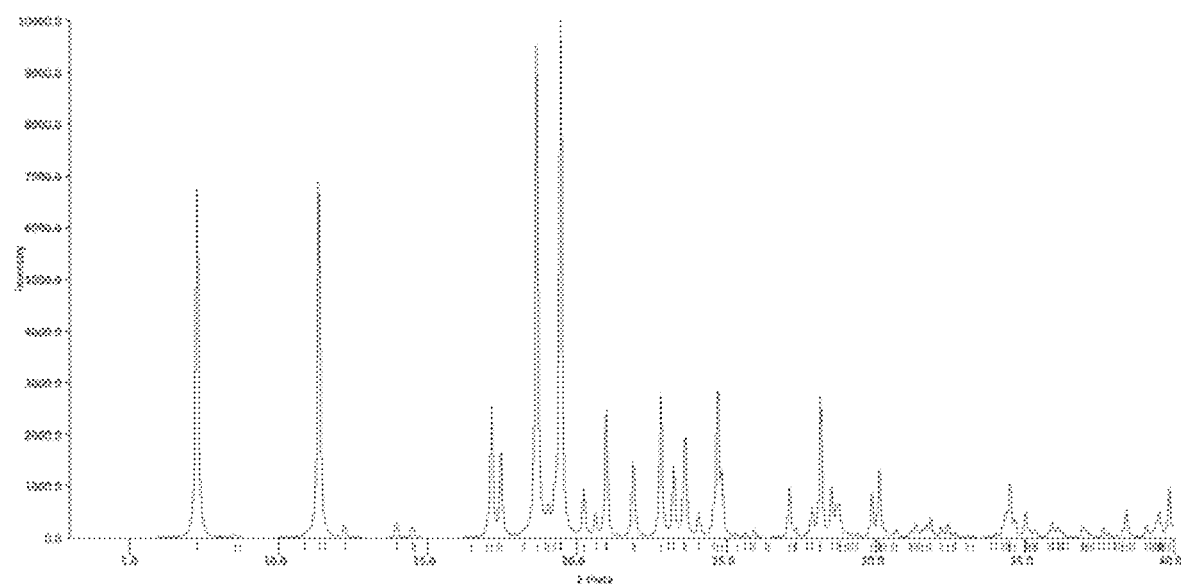
FIG. 26 is the calculated powder x-ray diffraction pattern of LISPRO, as described further in Example 7.

Crystals of LISPRO were characterized by FT-IR spectroscopy (Nicolet Avatar 320 FTIR, solid state) (FIG. 24), DSC (TA instrument 2920) (FIG. 25), powder x-ray diffraction (Bruker AXS D8, Cu radiation) (FIG. 26; calculated) and single crystal x-ray crystallography (Table 7). As can be seen from FIG. 26, major peaks were observed in the calculated powder x-ray diffraction pattern at approximately the following positions: 7.2, 11.3, 17.1, 18.6, 19.4, 20.9, 22.8, 24.7, 28.2°.

Figure 27:
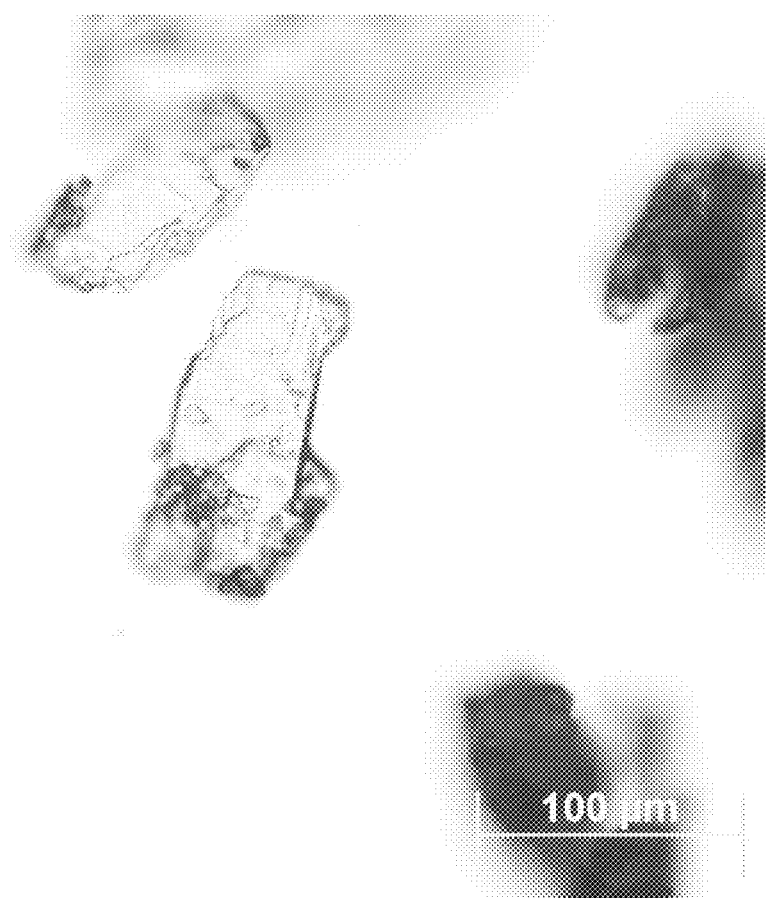
FIG. 27 is a digital microscope imager of LISPRO crystals, as described further in Example 7.

FIG. 27 shows a digital microscope image of LISPRO crystals.

The single crystal x-ray structural analysis reveals that LISPRO contains four lithium cations, four salicylate anions and four L-proline molecules in the unit cell. Each lithium cation is stabilized by tetrahedral coordination in square grid type waved 2-D layers extended in a and b directions. In the c direction, the layers are held together through pi-pi and CH . . . pi interaction of aromatic rings as well as weak CH . . . O interactions.

Figure 28:
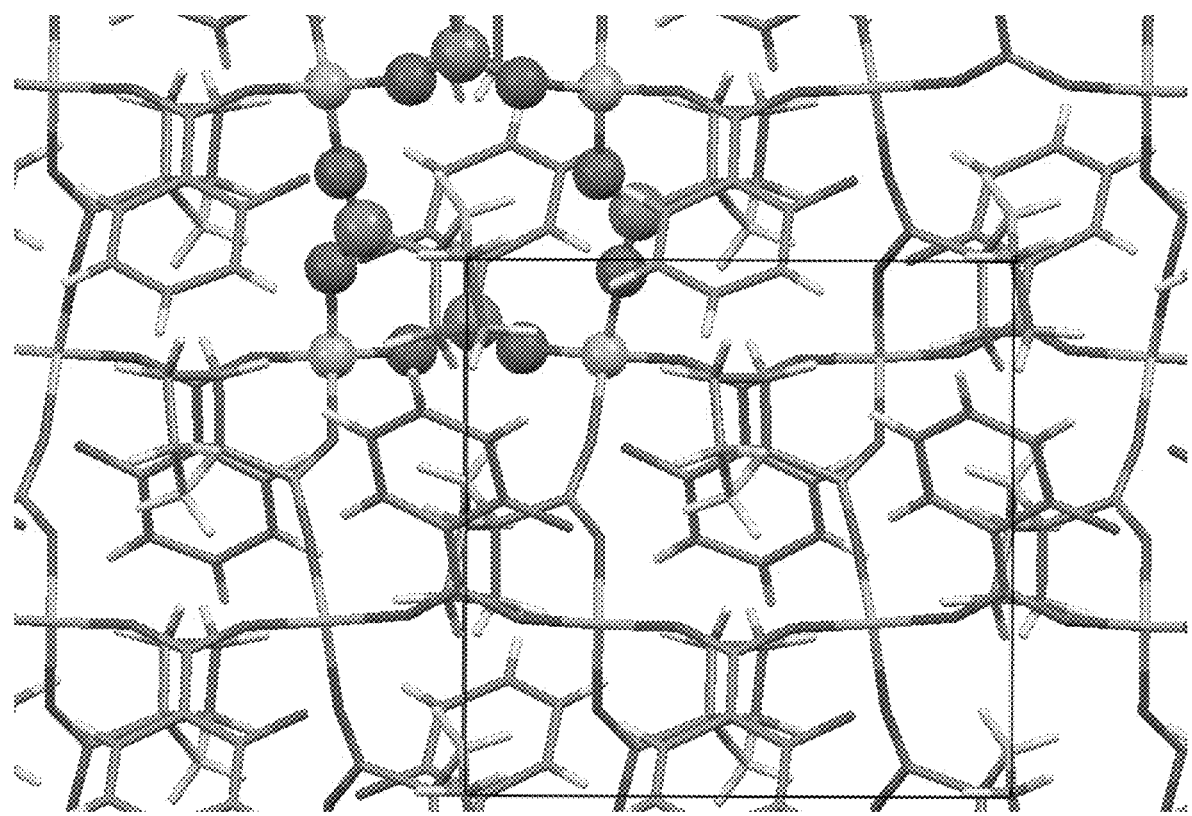
FIG. 28 is a crystal packing diagram of LISPRO, as described further in Example 7.

FIG. 28 shows a crystal packing diagram of LISPRO.

TABLE 7

Single crystal X-ray diffraction data for LISPRO
(Bruker-AXS APEX2 CCD diffractometer)

| Crystallographic data | |
| --- | --- |
| Empirical formula | $C_{24}H_{25}Li_2N_2O_{10}$ |
| Formula weight | 515.34 |
| Temperature | 293 (2) K |
| Wavelength | 1.54178 Å |
| Crystal system | Orthorhombic |
| Space group | $P2_1$ |
| Unit cell dimensions | a = 10.3591 (16) Å  α = 90.00° |
|  | b = 10.1545 (14) Å  β = 93.460 (10) |
|  | c = 12.173 (2) Å  γ = 90.00° |
| Volume | 1278.2 (4) Å$^3$ |
| Z | 2 |
| Density (calculated) | 1.339 Mg/m$^3$ |
| Reflections collected | 5567 |
| Independent reflections | 3498 [R(int) = 0.0431] |
| Final R indices [I > 2sigma(I)] | R1 = 0.0976, wR2 = 0.2651 |
| R indices (all data) | R1 = 0.1439, wR2 = 0.3124 |

Example 8

In this example, saccharinate was used as the counter ion in synthesizing novel lithium ionic cocrystals (ICCs) with amino acids: betaine (BTN) and sarcosine (SAR). The selection of saccharine as a counterion is justified because it is artificial sweetener and can be safely used as a food additive. Lithium saccharinate (LSC) is reported in open literature as 11/6 hydrate (Ong, T. T.; Kavuru, P.; Nguyen, T.; Cantwell, R.; Wojtas, Ł.; Zaworotko, M. J. *J Am Chem Soc*, 2011, 133, 9224-9227. (b) Zaworotko, M. J.; Shytle, R. D.; Teng, O. T.; Kavuru, P.; Cantwell, R. N.; Nguyen, T.; Smith, A. J. Preparation of lithium cocrystals for pharmaceuticals. WO 2012129568, 2012). Novel ICCs were synthesized from slow evaporation of water and mechanical grinding methods and the reaction mechanisms are as previously described herein. Two novel ionic cocrystals, LSCBTN (Lithium saccharinate betaine) and LSCSAR (Lithium saccharinate sarcosine) were characterized by single crystal X-ray diffraction, powder X-ray diffraction, thermogravimetric analysis and infrared spectroscopy One promising biological activity of lithium that has implications for treating neurodegenerative diseases (K. M. Boje and P. K. Arora, Brain research, 1992, 587, 250-256) and depression (M. Ghasemi, H. Sadeghipour, A. Mosleh, H. R. Sadeghipour, A. R. Mani and A. R. Dehpour, European neuropsychopharmacology: *the journal of the European College of Neuropsychopharmacology*, 2008, 18, 323-332) is the ability to attenuate microglial-produced nitric oxide. To determine if these new ICCs of LSC might offer more potent microglial modulatory bioactivity, a lipopolysaccharide (LPS)-activated microglia in vitro model of neuroinflammation was used. Smith et al. utilized this model and reported that another lithium ICC attenuated nitric oxide (NO) release from the LPS-stimulated microglia, a known bioactivity of lithium (Smith, A. J.; Kim, S. H.; Duggirala, N. K.; Jin, J.; Wojtas, Ł.; Ehrhart, J.; Giunta, B.; Tan, J.; Zaworotko, M. J.; Shytle, D. R., *Mol. Pharm.*). BV2 microglia cells were treated with LIC (LiCl), LSC (Lithium saccharinate), LSCBTN and LSCSAR at 12.5 and 25 mM in DMEM for 1 hour prior to activation of microglia by 100 ng/ml LPS. Nitrite ($NO^{2-}$), a stable breakdown product of NO, was measured in the media 24 hours later using a Griess Reagent System (Promega). Results are shown in FIG. 29.

Figure 29:
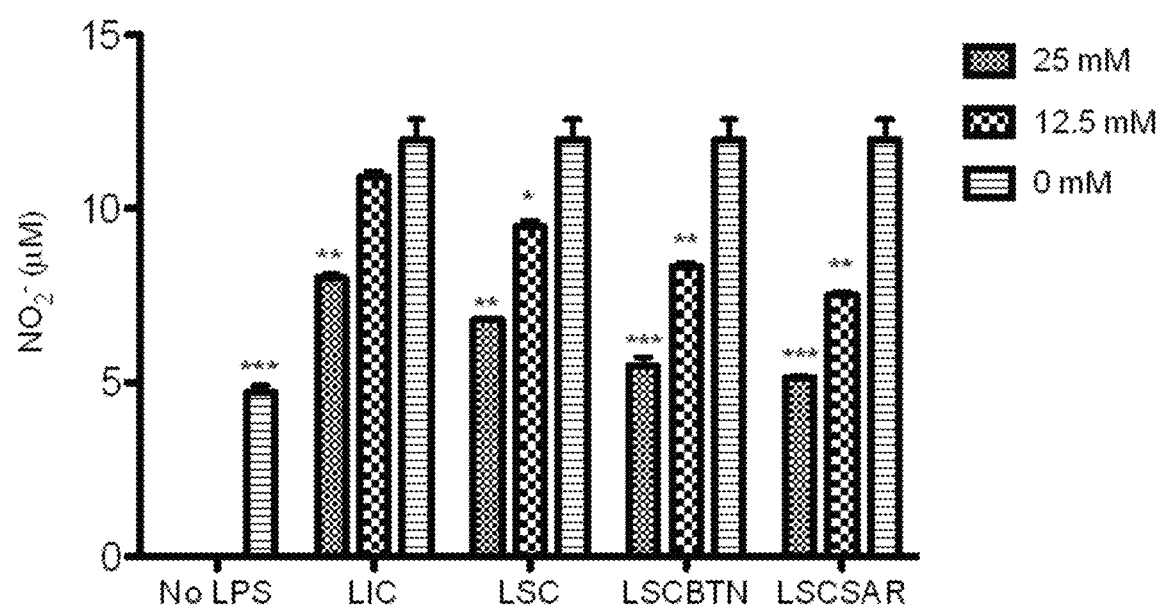
FIG. 29 is a graph depicting the results of an assay in which it was demonstrated that Lithium saccharinate (LSC) ionic cocrystals (ICCs) outperform lithium salts at abolishing NO production by LPS-activated microglia. Statistical significance from the no treatment (0 mM) with LPS control was assessed by t-tests (*$p<0.05$, $p<0.01$, *$p<0.001$) as described further in Example 8.

As illustrated in FIG. 29, LPS increased NO production by BV2 microglia. Further, all lithium treatment attenuated this pro-inflammatory response to different degrees. At 25 mM, both LSC ICCs completely inhibited NO production (*p>0.05 compared to No LPS control). Interestingly, LIC was found to be only partially effective. LSC outperformed LIC at both concentrations. However, both LSC ICCs outperformed the lithium salts (LIC and LSC) at all concentrations tested (**p<0.01). This suggests that the increased bioactivity is due either to synergistic actions of the amino acids or that these new ICCs of lithium are more permeable to BV2 microglia cells. It is presently believed that the latter is more likely and improved microglial modulatory activities that we observed. These findings are important and applicable to all crystal engineering-enabled drug discovery efforts.

What is claimed is:

1. A method of preparing a pharmaceutical composition containing a lithium cocrystal composition, the method comprising combining the lithium cocrystal composition with a pharmaceutically acceptable carrier or diluent, wherein the lithium cocrystal composition is produced by (1) mixing (i) a lithium salt comprising a conjugate base of an organic acid and (ii) a complementary neutral organic molecule in a solvent and (2) evaporating or cooling the solvent to form the lithium ionic cocrystal composition.

2. The method of claim 1 wherein the stoichiometric ratio of the complementary neutral organic compound to the lithium salt is 0.5:1 to 4:1, respectively.

3. The method of claim 1 wherein the stoichiometric ratio of the complementary neutral organic compound to the lithium salt is 0.5:1, respectively.

4. The method of claim 1 wherein the stoichiometric ratio of the complementary neutral organic compound to the lithium salt is 1:1, respectively.

5. The method of claim 1 wherein the stoichiometric ratio of the complementary neutral organic compound to the lithium salt is 2:1, respectively.

6. The method of any of claim 1 wherein the organic lithium ionic cocrystal composition is a solvate or a hydrate.

7. The method of claim 1 wherein the method comprises combining a lithium base, an organic acid, and the complementary neutral organic compound in the solvent.

8. The method of claim 1 wherein the lithium salt is produced by mixing lithium hydroxide with an organic acid.

9. The method of claim 1 wherein the method comprises introducing an organic anion lithium salt and the complementary neutral organic compound into the solvent.

10. The method of claim 1, wherein the organic acid is benzoic acid, salicylic acid, oxalic acid, or saccharin.

11. The method of claim 1, wherein the organic acid has a pKa in the range of 0 to 10.

12. The method of claim 1, wherein the complementary neutral organic molecule is a neutral zwitterionic compound, a xanthine, a polyphenol, a flavonoid, a sugar, or an amino acid.

13. The method of claim 1, wherein the solvent is a polar organic solvent.

14. The method of claim 1, wherein the solvent is acetone, acetonitrile, DMSO or an alcohol.

15. The method of claim 1, wherein the solvent is water.

16. The method of claim 1, wherein the conjugate base of the organic acid is acetate, adipate, diacetate, alginate, aminosalicylate, anhydromethylenecitrate, arecoline, arginine, ascorbate, asparatete, benzenesulfonate (benzene), benzoate, bicarbonate, bisulfate, bitartrate, butylbromide, butyrate, calcium edentate, calcium edentate, camphorate, camsylate (camphorsulfonate), citrate, dihydrochloride, edentate, edisylate (1,2-ethanedisulfonate), estolate (lauryl sulfate), esylate (ethanesulfonate), fumarate, gluceptate (glucoheptonate), gluconate, digluconate, glucuronate, glutamate, glycerophosphate, glucollylarsanilate (p-glycollamidophenylarsonate), hexylresorcinate, hydrabamine (N,N'-di(dehydroabietyl)ethylenediamine), hydroxynaphthoate, isethionate (2-hydroxyethanesulfonate), lactate, lactobionate, lysine, malate, maleate, mandelate, mesylate, methylbromide, methylenebis (salicylate), methylnitrate, methylsulfate, mucate, napdisylate (1,5-naphthalenedisulfonate), napsylate, oxalate, palmitate, pamoate (embonate), pantothenate, pectinate, phenylethyulbarbiturate, picrate, polygalacturonate, propionate, saccharinate, salicylate, stearate, subacetate, succinate, disuccinate, disuccinate, tannate, tartrate, terephthalate, teoclate (8-chlorotheophyllinate), thiocyanate, triethiodide, undecanoate, or xinafoate (1-hydroxy-2-naphthalenecarboxylate).

17. The method of claim 1, wherein the organic acid is acetylaminoacetic acid; N-acetyl-1-asparagine, N-acetylcystine, adamantoic acid, adipic acid, N-alkylsulfamates, anthraquinone-1,5-disulfonic acid, arabogalactan sulfate (arabino), arginine, aspartate, betaine, bis-2-carboxychromon-5-yloxy)alkanes, carnitine, 4-chloro-m-toluenesulfonic acid, decanoate, diacetyl sulfate, dibenzylethylenediamine, diethylamine, diguiacyl phosphate, diocytyl sulfosuccinate, embonic (pamoic) acid, fructose 1,6-diphosphoric acid, glucose 1-phosphoric acid, glucose 6-phosphoric acid, 1-glutamine, hydroxynaphthhoate, 2-(4-imidazolyl)ethylamine, isobutanolamine, lauryl sulfate, lysine, methanesulfonic acid, N-methylglucamine, N-methylpiperazine, morphonine, 2-naphthalenesulfonic acid, octanoate, probenecid, tannic acid, theobromine acetic acid, or 3,4,5-trimethoxybenzoate, tromethamine.

18. The method of claim 1, wherein the lithium cocrystal composition has the formula LiX.aM, or a solvate or hydrate thereof, wherein
X is a conjugate base of an organic acid,
M is the complementary neutral organic compound comprising neutral zwitterionic compound, a xanthine, a polyphenol, a flavonoid, or an amino acid; and
a is from 0.5 to 4.

19. The method of claim 1, wherein the lithium cocrystal composition has the formula LiX.aM.bS wherein
X is a conjugate base of an organic acid;
M is the complementary neutral organic compound comprising neutral zwitterionic compound, a xanthine, a polyphenol, a flavonoid, or an amino acid;
S is solvent or water;
a is from 0.5 to 4; and
b is 0, 0.5, 1, 1.5, 2, 2.5 or 3.

* * * * *